(12) United States Patent
Nakagawara

(10) Patent No.: US 7,214,782 B2
(45) Date of Patent: May 8, 2007

(54) NUCLEIC ACID OF NOVEL HUMAN KINESIN-RELATED GENE PROTEIN ENCODED BY THE NUCLEIC ACID PEPTIDE FRAGMENT THEREOF AND ANTICANCER AGENTS COMPRISING THE NUCLEIC ACID AND THE LIKE

(75) Inventor: Akira Nakagawara, Chiba (JP)

(73) Assignees: Hisamitsu Pharmaceutical Co., Inc., Saga (JP); Chiba-Prefecture, Chiba (JP)

( * ) Notice: Subject to any disclaimer, the term of this patent is extended or adjusted under 35 U.S.C. 154(b) by 517 days.

(21) Appl. No.: 10/381,792

(22) PCT Filed: Oct. 1, 2001

(86) PCT No.: PCT/JP01/08635

§ 371 (c)(1),
(2), (4) Date: Sep. 22, 2003

(87) PCT Pub. No.: WO02/26965

PCT Pub. Date: Apr. 4, 2002

(65) Prior Publication Data

US 2004/0072778 A1    Apr. 15, 2004

(51) Int. Cl.
C07H 21/04    (2006.01)

(52) U.S. Cl. ............... 536/23.1; 536/23.5; 530/350

(58) Field of Classification Search ............ 536/23.5, 536/23.1, 24.31, 24.33, 24.5; 530/350, 300; 514/2, 44
See application file for complete search history.

(56) References Cited

U.S. PATENT DOCUMENTS

2001/0053519 A1* 12/2001 Fodor et al. .................. 435/6

FOREIGN PATENT DOCUMENTS

WO    WO 00/63375    10/2000

OTHER PUBLICATIONS

Nakagawara et al. (Med. Pediatr. Oncol. Dec. 2000; 35 (6): 516-521).*
Yang et al. (Oncogene. 2001; 20: 5075-5083).*
Skolnick et al. (Trends in Biotechnology 2000; 18: 34-39).*
Chen et al. (Int. J. Oncol. 2003; 23: 737-744).*
Bowie et al. (Science. 1990; 257: 1306-1310).*
Burgess et al. (Journal of Cell Biology 1990; 111: 2129-2138).*
Lazar et al. (Molecular and Cellular Biology, 1988, 8: 1247-1252).*
Luque et al. (Biochemistry. Nov. 19, 2002; 41 (46): 13663-13671).*
Vucic et al. (J. Biol. Chem. Dec. 18, 1998; 273 (51): 33915-33921).*
Takada et al. (Mol. Endocrinol. 2000; 14 (5): 733-740).*
Guo et al. (Proc. Natl. Acad. Sci. USA Jun. 22, 2004; 101 (25): 9205-9210).*
Gura (Science. 1997; 278: 1041-1042).*
Saijo et al. (Cancer Sci. Oct. 2004; 95 (10): 772-776).*
Kelland (Eur. J. Cancer. Apr. 2004; 40 (6): 827-836).*
Bergers et al. (Current Opinion in Genetics and Development. 2000; 10: 120-127).*
Olsen et al. (Cell Growth Differ. Apr. 1997; 8 (4): 417-423).*
Presneau et al. (Curr. Mol. Med. Nov. 2003; 3 (7): 605-629).*
Zenklusen et al. (Oncogene. 2000; 19: 1729-1733).*
Boehringer Mannheim Biochemicals, 1994 Catalog (No. 1034 731/1006 924), p. 93.*
Nakagawara (Database GENEMBL Accession No. AB017133 (Oct. 2, 2001).*
Hirokawa et al., *Submolecular Domains of Bovine Brain Kinesin Identified by Electron Microscopy and Monoclonal Antibody Decoration*, Cell, vol. 56, pp. 867-878 (Mar. 10, 1989).
Cyr et al., *Molecular genetics of kinesin light chains*: Generation of isoforms by alternative splicing, Proc. Natl. Acad. Sci. USA, vol. 88, pp. 10114-10118 (Nov. 1991) Cell Biology.
Eyer et al., *Pathogenesis of two axonopathies does not require axonal neurofilaments*, Nature, vol. 391, pp. 584-587 (Feb. 5, 1998).
Gibbons, *Dyein Family of Motor Proteins: Present Status and Future Questions*, Cell Motility and the Cytoskeleton, 32:136-144 (1995).
Hirokawa, *Kinesin and Dynein Superfamily Proteins and the Mechanism of Organelle Transport*, Frontiers in Cell Biology: Articles, Science, vol. 279 (Jan. 23, 1998).
Aizawa et al., *Kinesin Family in Murine Central Nervous System*, The Journal of Cell Biology, vol. 119, No. 5, pp. 1287-1296 (Dec. 1992).
Niclas, et al., *Cloning and Localization of a Conventional Kinesin Motor Expressed Exclusively in Neurons*, Neuron, vol. 12, pp. 1059-1072 (May 1994).
Okada, et al., *The Neuron-Specific Kinesin Superfamily Protein KIF1A Is a Unique Monomeric Motor for Anterograde Axonal Transport of Synaptic Vesicle Precursors*, Cell. vol. 81, pp. 769-780 (Jun. 2, 1995).
Nangaku, et al., *KIF1B, a Novel Microtubule Plus End-Directed Monomeric Motor Protein for Transport of Mitochondria*, Cell, vol. 79, pp. 1209-1220 (Dec. 30, 1994).
Yamazaki, et al., *Cloning and characterization of KAP3: A novel kinesin superfamily-associated protein of KIF3A/3B*, Proc. Natl. Acad. Sci. USA, vol. 93, pp. 8443-8448 (Aug. 1996).
Shingyoji, et al., *Dynein arms are oscillating force generators*, Nature vol. 393, pp. 711-714 (Jun. 18, 1998).

(Continued)

*Primary Examiner*—Stephen L. Rawlings
(74) *Attorney, Agent, or Firm*—Fitch, Even, Tabin & Flannery

(57) ABSTRACT

There are provided base sequence data for human kinesin-related genes with a motor domain, as well as information relating to the functions of the proteins encoded by the human kinesin-related gene and the motor domain-lacking human kinesin-related gene, which data may be utilized for diagnosis (for example, judging prognosis of neuroblastoma) and treatment (particularly as antisense nucleic acids for malignant tumors).

4 Claims, 7 Drawing Sheets

OTHER PUBLICATIONS

Noda, et al., *KIF2 Is A New Microtubule-based Anterograde Motor That Transports Membranous Organelles Distinct From Those Carried By Kinesin Heavy Chain or KIF3A/B*, The Journal of Cell Biology, vol. 129, No. 1, pp. 157-167 (Apr. 1, 1995).

Saito et al., *KIFC2 Is A Novel Neuron-Specific C-Terminal Type Kinesin Superfamily Motor for Dendritic Transport of Multivesicular Body-Like Organelles*, Neuron, vol. 18, pp. 425-438 (Mar. 1997).

Nagase et al., *Prediction of the Coding Sequences of Unidentified Human Genes. IX. The Complete Sequences of 100 New cDNA Clones from Brain Which Can Code for Large Proteins in vitro*, DNA Research 5, pp. 31-39 (1998).

Nagi et al., *Identification of the Full-Length KIAA0591 Gene Encoding a Novel Kinesin-Related Protein Which is Mapped To The Neuroblastoma Suppressor Gene Locus at 1p36.2*, International Journal of Oncology, vol. 16, pp. 907-916 (2000).

Darnell et al., Molecular Cell Biology, Second Edition 24, p. 963 (1993).

Naldini et al., *In Vivo Gene Delivery and Stable Transduction of Nondividing Cells by a Lentiviral Vector*, Science, vol. 272, pp. 263-267 (Apr. 12, 1996).

Sanger et al., *DNA Sequencing With Chain-Terminating Inhibitors*, Proc. Natl. Acad. Sci. USA, vol. 74, No. 12, pp. 5463-5467 (Dec. 1977).

Nagai et al., *Identification of the Full-Length KIAA0591 Gene Encoding a Novel Kinesin-Related Protein Which is Mapped To The Neuroblastoma Suppressor Gene Locus at 1p36.2*, International Journal of Oncology, vol. 16, pp. 907-916 (2000).

Gong et al. *A Novel Mouse Kinesin of the UNC-104/KIF1 Subfamily Encoded by the Kit 1b Gene*, Gene 239, pp. 117-127 (1999).

Garkavtsev et al., *Suppression of the Novel Growth Inhibitor $p33^{ING1}$ Promotes Neoplastic Transformation*, Nature Genetics, vol. 14 (Dec. 1996).

Yang et al., "Identification. Partial Characterization, and Genetic Mapping of Kinesin-like Protein Genes in Mouse", Genomics. 45:123-131 (Academic Press 1997).

Nangaku et al., KIF1B, "A Novel Microtubule Plus End-Directed Monomeric Motor Protein for Transport of Mitochondria", Cell, 79:1209-1220(Cell Press 1994).

Nakagawa et al., "Identification and classification of 16 new kinesin superfamily (KIF) proteins in mouse genome", Proc. Nat'l. Acad. Sci., 94:9654-9659 (Sep. 1994).

Nagase et al., "Prediction of the Coding Sequences of Unidentified Human Genes. IX. The Complete Sequences of 100 New CDMA Clones From Brain Which Can Code for Large Proteins In Vitro". DNA Research, 5:31-39 (Universal Academic Press 1998).

Mariko Nagai et al., "Identification of the full-length KIAA0591 gene encoding a novel kinesin-related protein which is mapped to the neuroblastoma suppressor gene locus at 1p36.2," International Journal of Oncology, vol. 16, No. 5, pp. 907-916, May 2000.

\* cited by examiner

SEQUENCE LISTING

<160> NUMBER OF SEQ ID NOS: 7

<210> SEQ ID NO 1
<211> LENGTH: 1381
<212> TYPE: PRT
<213> ORGANISM: Homo sapiens

<400> SEQUENCE: 1

Met Gly Ser Leu Thr Ser Ser Pro Ser Ser Cys Ser Leu Ser Ser Gln
 1               5                  10                  15

Val Gly Leu Thr Ser Val Thr Ser Ile Gln Glu Arg Ile Met Ser Thr
            20                  25                  30

-continued

```
Pro Gly Gly Glu Glu Ala Ile Glu Arg Leu Lys Glu Ser Glu Lys Ile
         35                  40                  45

Ile Ala Glu Leu Asn Glu Thr Trp Glu Glu Lys Leu Arg Lys Thr Glu
     50                  55                  60

Ala Ile Arg Met Glu Arg Glu Ala Leu Leu Ala Glu Met Gly Val Ala
 65                  70                  75                  80

Ile Arg Glu Asp Gly Gly Thr Leu Gly Val Phe Ser Pro Lys Lys Thr
                 85                  90                  95

Pro His Leu Val Asn Leu Asn Glu Asp Pro Leu Met Ser Glu Cys Leu
                100                 105                 110

Leu Tyr Tyr Ile Lys Asp Gly Ile Thr Arg Val Gly Gln Ala Asp Ala
            115                 120                 125

Glu Arg Arg Gln Asp Ile Val Leu Ser Gly Ala His Ile Lys Glu Glu
        130                 135                 140

His Cys Ile Phe Arg Ser Glu Arg Ser Asn Ser Gly Glu Val Ile Val
145                 150                 155                 160

Thr Leu Glu Pro Cys Glu Arg Ser Glu Thr Tyr Val Asn Gly Lys Arg
                165                 170                 175

Val Ser Gln Pro Val Gln Leu Arg Ser Gly Asn Arg Ile Ile Met Gly
                180                 185                 190

Lys Asn His Val Phe Arg Phe Asn His Pro Glu Gln Ala Arg Ala Glu
            195                 200                 205

Arg Glu Lys Thr Pro Ser Ala Glu Thr Pro Ser Glu Pro Val Asp Trp
        210                 215                 220

Thr Phe Ala Gln Arg Glu Leu Leu Lys Gln Gly Ile Asp Met Lys
225                 230                 235                 240

Gln Glu Met Glu Lys Arg Leu Gln Glu Met Glu Ile Leu Tyr Lys Lys
                245                 250                 255

Glu Lys Glu Glu Ala Asp Leu Leu Leu Glu Gln Gln Arg Leu Asp Tyr
                260                 265                 270

Glu Ser Lys Leu Gln Ala Leu Gln Lys Gln Val Glu Thr Arg Ser Leu
            275                 280                 285

Ala Ala Glu Thr Thr Glu Glu Glu Glu Glu Glu Glu Val Pro Trp
        290                 295                 300

Thr Gln His Glu Phe Glu Leu Ala Gln Trp Ala Phe Arg Lys Trp Lys
305                 310                 315                 320

Ser His Gln Phe Thr Ser Leu Arg Asp Leu Leu Trp Gly Asn Ala Val
                325                 330                 335

Tyr Leu Lys Glu Ala Asn Ala Ile Ser Val Glu Leu Lys Lys Lys Val
            340                 345                 350

Gln Phe Gln Phe Val Leu Leu Thr Asp Thr Leu Tyr Ser Pro Leu Pro
        355                 360                 365

Pro Glu Leu Leu Pro Thr Glu Met Glu Lys Thr His Glu Asp Arg Pro
    370                 375                 380

Phe Pro Arg Thr Val Val Ala Val Glu Val Gln Asp Leu Lys Asn Gly
385                 390                 395                 400

Ala Thr His Tyr Trp Ser Leu Glu Lys Leu Lys Gln Arg Leu Asp Leu
                405                 410                 415

Met Arg Glu Met Tyr Asp Arg Ala Gly Glu Met Ala Ser Ser Ala Gln
            420                 425                 430

Asp Glu Ser Glu Thr Thr Val Thr Gly Ser Asp Pro Phe Tyr Asp Arg
        435                 440                 445
```

-continued

```
Phe His Trp Phe Lys Leu Val Gly Ser Ser Pro Ile Phe His Gly Cys
    450                 455                 460

Val Asn Glu Arg Leu Ala Asp Arg Thr Pro Ser Pro Thr Phe Ser Thr
465                 470                 475                 480

Ala Asp Ser Asp Ile Thr Glu Leu Ala Asp Glu Gln Gln Asp Glu Met
                485                 490                 495

Glu Asp Phe Asp Asp Glu Ala Phe Val Asp Asp Ala Gly Ser Asp Ala
            500                 505                 510

Gly Thr Glu Glu Gly Ser Asp Leu Phe Ser Asp Gly His Asp Pro Phe
        515                 520                 525

Tyr Asp Arg Ser Pro Trp Phe Ile Leu Val Gly Arg Ala Phe Val Tyr
    530                 535                 540

Leu Ser Asn Leu Leu Tyr Pro Val Pro Leu Ile His Arg Val Ala Ile
545                 550                 555                 560

Val Ser Glu Lys Gly Glu Val Arg Gly Phe Leu Arg Val Ala Val Gln
                565                 570                 575

Ala Ile Ala Ala Asp Glu Glu Ala Pro Asp Tyr Gly Ser Gly Ile Arg
            580                 585                 590

Gln Ser Gly Thr Ala Lys Ile Ser Phe Asp Asn Glu Tyr Phe Asn Gln
        595                 600                 605

Ser Asp Phe Ser Ser Val Ala Met Thr Arg Ser Gly Leu Ser Leu Glu
    610                 615                 620

Glu Leu Arg Ile Val Glu Gly Gln Gly Gln Ser Ser Glu Val Ile Thr
625                 630                 635                 640

Pro Pro Glu Glu Ile Ser Arg Ile Asn Asp Leu Asp Leu Lys Ser Ser
                645                 650                 655

Thr Leu Leu Asp Gly Lys Met Val Met Glu Gly Phe Ser Glu Glu Ile
            660                 665                 670

Gly Asn His Leu Lys Leu Gly Ser Ala Phe Thr Phe Arg Val Thr Val
        675                 680                 685

Leu Gln Ala Ser Gly Ile Leu Pro Glu Tyr Ala Asp Ile Phe Cys Gln
    690                 695                 700

Phe Asn Phe Leu His Arg His Asp Glu Ala Phe Ser Thr Glu Pro Leu
705                 710                 715                 720

Lys Asn Asn Gly Arg Gly Ser Pro Leu Ala Phe Tyr His Val Gln Asn
                725                 730                 735

Ile Ala Val Glu Ile Thr Glu Ser Phe Val Asp Tyr Ile Lys Thr Lys
            740                 745                 750

Pro Ile Val Phe Glu Val Phe Gly His Tyr Gln Gln His Pro Leu His
        755                 760                 765

Leu Gln Gly Gln Glu Leu Asn Ser Pro Gln Pro Cys Arg Arg Phe
    770                 775                 780

Phe Pro Pro Met Pro Leu Ser Lys Pro Val Pro Ala Thr Lys Leu
785                 790                 795                 800

Asn Thr Met Ser Lys Thr Ser Leu Gly Gln Ser Met Ser Lys Tyr Asp
                805                 810                 815

Leu Leu Val Trp Phe Glu Ile Ser Leu Glu Pro Thr Gly Glu Tyr
            820                 825                 830

Ile Pro Ala Val Val Asp His Thr Ala Gly Leu Pro Cys Gln Gly Thr
        835                 840                 845

Phe Leu Leu His Gln Gly Ile Gln Arg Ile Thr Val Thr Ile Ile
    850                 855                 860

His Glu Lys Gly Ser Glu Leu His Trp Lys Asp Val Arg Glu Leu Val
```

-continued

```
            865                 870                 875                 880
Val Gly Arg Ile Arg Asn Lys Pro Glu Val Asp Glu Ala Ala Val Asp
                    885                 890                 895
Ala Ile Leu Ser Leu Asn Ile Ile Ser Ala Lys Tyr Leu Lys Ser Ser
                900                 905                 910
His Asn Ser Ser Arg Thr Phe Tyr Arg Phe Glu Ala Val Trp Asp Ser
                915                 920                 925
Ser Leu His Asn Ser Leu Leu Leu Asn Arg Val Thr Pro Tyr Gly Glu
        930                 935                 940
Lys Ile Tyr Met Thr Leu Ser Ala Tyr Leu Glu Leu Asp His Cys Ile
945                 950                 955                 960
Gln Pro Ala Val Ile Thr Lys Asp Val Cys Met Val Phe Tyr Ser Arg
                965                 970                 975
Asp Ala Lys Ile Ser Pro Pro Arg Ser Leu Arg Ser Leu Phe Gly Ser
                980                 985                 990
Gly Tyr Ser Lys Ser Pro Asp Ser Asn Arg Val Thr Gly Ile Tyr Glu
                995                 1000                1005
Leu Ser Leu Cys Lys Met Ser Asp Thr Gly Ser Pro Gly Met Gln Arg
        1010                1015                1020
Arg Arg Arg Lys Ile Leu Asp Thr Ser Val Ala Tyr Val Arg Gly Glu
1025                1030                1035                1040
Glu Asn Leu Ala Gly Trp Arg Pro Arg Gly Asp Ser Leu Ile Leu Glu
                1045                1050                1055
His Gln Trp Glu Leu Glu Lys Leu Glu Leu Leu His Glu Val Glu Lys
                1060                1065                1070
Thr Arg His Phe Leu Leu Leu Arg Glu Arg Leu Gly Asp Ser Ile Pro
        1075                1080                1085
Lys Ser Leu Ser Asp Ser Leu Ser Pro Ser Leu Ser Ser Gly Thr Leu
        1090                1095                1100
Ser Thr Ser Thr Ser Ile Ser Ser Gln Ile Ser Thr Thr Thr Phe Glu
1105                1110                1115                1120
Ser Ala Ile Thr Pro Ser Glu Ser Ser Gly Tyr Asp Ser Gly Asp Ile
                1125                1130                1135
Glu Ser Leu Val Asp Arg Glu Lys Glu Leu Ala Thr Lys Cys Leu Gln
                1140                1145                1150
Leu Leu Thr His Thr Phe Asn Arg Glu Phe Ser Gln Val His Gly Ser
            1155                1160                1165
Val Ser Asp Cys Lys Leu Ser Asp Ile Ser Pro Ile Gly Arg Asp Pro
        1170                1175                1180
Ser Glu Ser Ser Phe Ser Ser Ala Thr Leu Thr Pro Ser Ser Thr Cys
1185                1190                1195                1200
Pro Ser Leu Val Asp Ser Arg Ser Asn Ser Leu Asp Gln Lys Thr Pro
                1205                1210                1215
Glu Ala Asn Ser Arg Ala Ser Ser Pro Cys Pro Glu Phe Glu Gln Phe
                1220                1225                1230
Gln Ile Val Pro Ala Val Glu Thr Pro Tyr Leu Ala Arg Ala Gly Lys
            1235                1240                1245
Asn Glu Phe Leu Asn Leu Val Pro Asp Ile Glu Glu Ile Arg Pro Ser
                1250                1255                1260
Ser Val Val Ser Lys Lys Gly Tyr Leu His Phe Lys Glu Pro Leu Tyr
1265                1270                1275                1280
Ser Asn Trp Ala Lys His Phe Val Val Arg Arg Pro Tyr Val Phe
                1285                1290                1295
```

-continued

```
Ile Tyr Asn Ser Asp Lys Asp Pro Val Glu Arg Gly Ile Ile Asn Leu
            1300                1305                1310

Ser Thr Ala Gln Val Glu Tyr Ser Glu Asp Gln Gln Ala Met Val Lys
        1315                1320                1325

Thr Pro Asn Thr Phe Ala Val Cys Thr Lys His Arg Gly Val Leu Leu
        1330                1335                1340

Gln Ala Leu Asn Asp Lys Asp Met Asn Asp Trp Leu Tyr Ala Phe Asn
1345                1350                1355                1360

Pro Leu Leu Ala Gly Thr Ile Arg Ser Lys Leu Ser Arg Arg Cys Pro
                1365                1370                1375

Ser Gln Ser Lys Tyr
            1380

<210> SEQ ID NO 2
<211> LENGTH: 1823
<212> TYPE: PRT
<213> ORGANISM: Homo sapiens

<400> SEQUENCE: 2

Met Ser Gly Ala Ser Val Lys Val Ala Val Arg Val Arg Pro Phe Asn
 1               5                  10                  15

Ser Arg Glu Thr Ser Lys Glu Ser Lys Cys Ile Ile Gln Met Gln Gly
            20                  25                  30

Asn Ser Thr Ser Ile Ile Asn Pro Lys Asn Pro Lys Glu Ala Pro Lys
        35                  40                  45

Ser Phe Ser Phe Asp Tyr Ser Tyr Trp Ser His Thr Ser Pro Glu Asp
    50                  55                  60

Pro Cys Phe Ala Ser Gln Asn Arg Val Tyr Asn Asp Ile Gly Lys Glu
65                  70                  75                  80

Met Leu Leu His Ala Phe Glu Gly Tyr Asn Val Cys Ile Phe Ala Tyr
                85                  90                  95

Gly Gln Thr Gly Ala Gly Lys Ser Tyr Thr Met Met Gly Lys Gln Glu
            100                 105                 110

Glu Ser Gln Ala Gly Ile Ile Pro Gln Leu Cys Glu Glu Leu Phe Glu
        115                 120                 125

Lys Ile Asn Asp Asn Cys Asn Glu Glu Met Ser Tyr Ser Val Glu Val
    130                 135                 140

Ser Tyr Met Glu Ile Tyr Cys Glu Arg Val Arg Asp Leu Leu Asn Pro
145                 150                 155                 160

Lys Asn Lys Gly Asn Leu Arg Val Arg Glu His Pro Leu Leu Gly Pro
                165                 170                 175

Tyr Val Glu Asp Leu Ser Lys Leu Ala Val Thr Ser Tyr Thr Asp Ile
            180                 185                 190

Ala Asp Leu Met Asp Ala Gly Asn Lys Ala Arg Thr Val Ala Ala Thr
        195                 200                 205

Asn Met Asn Glu Thr Ser Ser Arg Ser His Ala Val Phe Thr Ile Val
    210                 215                 220

Phe Thr Gln Lys Lys His Asp Asn Glu Thr Asn Leu Ser Thr Glu Lys
225                 230                 235                 240

Val Ser Lys Ile Ser Leu Val Asp Leu Ala Gly Ser Glu Arg Ala Asp
                245                 250                 255

Ser Thr Gly Ala Lys Gly Thr Arg Leu Lys Glu Gly Ala Asn Ile Asn
            260                 265                 270

Lys Ser Leu Thr Thr Leu Gly Lys Val Ile Ser Ala Leu Ala Glu Val
```

-continued

```
                275                 280                 285
Asp Asn Cys Thr Ser Lys Ser Lys Lys Lys Lys Thr Asp Phe Ile
        290                 295                 300

Pro Tyr Arg Asp Ser Val Leu Thr Trp Leu Leu Arg Glu Asn Leu Gly
305                 310                 315                 320

Gly Asn Ser Arg Thr Ala Met Val Ala Ala Leu Ser Pro Ala Asp Ile
                325                 330                 335

Asn Tyr Asp Glu Thr Leu Ser Thr Leu Arg Tyr Ala Asp Arg Ala Lys
                340                 345                 350

Gln Ile Lys Cys Asn Ala Val Ile Asn Glu Gly Pro Asn Ala Lys Leu
                355                 360                 365

Val Arg Glu Leu Lys Glu Val Thr Arg Leu Lys Asp Leu Leu Arg
    370                 375                 380

Ala Gln Gly Leu Gly Asp Ile Ile Asp Ile Asp Pro Leu Ile Asp Asp
385                 390                 395                 400

Tyr Ser Gly Ser Gly Ser Lys Tyr Leu Lys Asp Phe Gln Asn Asn Lys
                405                 410                 415

His Arg Tyr Leu Leu Ala Ser Glu Asn Gln Arg Pro Gly His Phe Ser
                420                 425                 430

Thr Ala Ser Met Gly Ser Leu Thr Ser Ser Pro Ser Ser Cys Ser Leu
                435                 440                 445

Ser Ser Gln Val Gly Leu Thr Ser Val Thr Ser Ile Gln Glu Arg Ile
    450                 455                 460

Met Ser Thr Pro Gly Gly Glu Glu Ala Ile Glu Arg Leu Lys Glu Ser
465                 470                 475                 480

Glu Lys Ile Ile Ala Glu Leu Asn Glu Thr Trp Glu Glu Lys Leu Arg
                485                 490                 495

Lys Thr Glu Ala Ile Arg Met Glu Arg Glu Ala Leu Leu Ala Glu Met
                500                 505                 510

Gly Val Ala Ile Arg Glu Asp Gly Gly Thr Leu Gly Val Phe Ser Pro
                515                 520                 525

Lys Lys Thr Pro His Leu Val Asn Leu Asn Glu Asp Pro Leu Met Ser
    530                 535                 540

Glu Cys Leu Leu Tyr Tyr Ile Lys Asp Gly Ile Thr Arg Val Gly Gln
545                 550                 555                 560

Ala Asp Ala Glu Arg Arg Gln Asp Ile Val Leu Ser Gly Ala His Ile
                565                 570                 575

Lys Glu Glu His Cys Ile Phe Arg Ser Glu Arg Ser Asn Ser Gly Glu
                580                 585                 590

Val Ile Val Thr Leu Glu Pro Cys Glu Arg Ser Glu Thr Tyr Val Asn
    595                 600                 605

Gly Lys Arg Val Ser Gln Pro Val Gln Leu Arg Ser Gly Asn Arg Ile
    610                 615                 620

Ile Met Gly Lys Asn His Val Phe Arg Phe Asn His Pro Glu Gln Ala
625                 630                 635                 640

Arg Ala Glu Arg Glu Lys Thr Pro Ser Ala Glu Thr Pro Ser Glu Pro
                645                 650                 655

Val Asp Trp Thr Phe Ala Gln Arg Glu Leu Leu Glu Lys Gln Gly Ile
                660                 665                 670

Asp Met Lys Gln Glu Met Glu Lys Arg Leu Gln Glu Met Glu Ile Leu
        675                 680                 685

Tyr Lys Lys Glu Lys Glu Glu Ala Asp Leu Leu Leu Glu Gln Gln Arg
    690                 695                 700
```

```
Leu Asp Tyr Glu Ser Lys Leu Gln Ala Leu Gln Lys Gln Val Glu Thr
705                 710                 715                 720

Arg Ser Leu Ala Ala Glu Thr Thr Glu Glu Glu Glu Glu Glu Glu Glu
                725                 730                 735

Val Pro Trp Thr Gln His Glu Phe Glu Leu Ala Gln Trp Ala Phe Arg
                740                 745                 750

Lys Trp Lys Ser His Gln Phe Thr Ser Leu Arg Asp Leu Leu Trp Gly
                755                 760                 765

Asn Ala Val Tyr Leu Lys Glu Ala Asn Ala Ile Ser Val Glu Leu Lys
                770                 775                 780

Lys Lys Val Gln Phe Gln Phe Val Leu Leu Thr Asp Thr Leu Tyr Ser
785                 790                 795                 800

Pro Leu Pro Pro Glu Leu Leu Pro Thr Glu Met Glu Lys Thr His Glu
                805                 810                 815

Asp Arg Pro Phe Pro Arg Thr Val Val Ala Val Glu Val Gln Asp Leu
                820                 825                 830

Lys Asn Gly Ala Thr His Tyr Trp Ser Leu Glu Lys Leu Lys Gln Arg
                835                 840                 845

Leu Asp Leu Met Arg Glu Met Tyr Asp Arg Ala Gly Glu Met Ala Ser
                850                 855                 860

Ser Ala Gln Asp Glu Ser Glu Thr Thr Val Thr Gly Ser Asp Pro Phe
865                 870                 875                 880

Tyr Asp Arg Phe His Trp Phe Lys Leu Val Gly Ser Ser Pro Ile Phe
                885                 890                 895

His Gly Cys Val Asn Glu Arg Leu Ala Asp Arg Thr Pro Ser Pro Thr
                900                 905                 910

Phe Ser Thr Ala Asp Ser Asp Ile Thr Glu Leu Ala Asp Glu Gln Gln
                915                 920                 925

Asp Glu Met Glu Asp Phe Asp Asp Glu Ala Phe Val Asp Asp Ala Gly
                930                 935                 940

Ser Asp Ala Gly Thr Glu Glu Gly Ser Asp Leu Phe Ser Asp Gly His
945                 950                 955                 960

Asp Pro Phe Tyr Asp Arg Ser Pro Trp Phe Ile Leu Val Gly Arg Ala
                965                 970                 975

Phe Val Tyr Leu Ser Asn Leu Leu Tyr Pro Val Pro Leu Ile His Arg
                980                 985                 990

Val Ala Ile Val Ser Glu Lys Gly Glu Val Arg Gly Phe Leu Arg Val
                995                 1000                1005

Ala Val Gln Ala Ile Ala Ala Asp Glu Glu Ala Pro Asp Tyr Gly Ser
                1010                1015                1020

Gly Ile Arg Gln Ser Gly Thr Ala Lys Ile Ser Phe Asp Asn Glu Tyr
1025                1030                1035                1040

Phe Asn Gln Ser Asp Phe Ser Ser Val Ala Met Thr Arg Ser Gly Leu
                1045                1050                1055

Ser Leu Glu Glu Leu Arg Ile Val Glu Gly Gln Gly Gln Ser Ser Glu
                1060                1065                1070

Val Ile Thr Pro Pro Glu Glu Ile Ser Arg Ile Asn Asp Leu Asp Leu
                1075                1080                1085

Lys Ser Ser Thr Leu Leu Asp Gly Lys Met Val Met Glu Gly Phe Ser
                1090                1095                1100

Glu Glu Ile Gly Asn His Leu Lys Leu Gly Ser Ala Phe Thr Phe Arg
1105                1110                1115                1120
```

-continued

```
Val Thr Val Leu Gln Ala Ser Gly Ile Leu Pro Glu Tyr Ala Asp Ile
            1125                1130                1135

Phe Cys Gln Phe Asn Phe Leu His Arg His Asp Glu Ala Phe Ser Thr
            1140                1145                1150

Glu Pro Leu Lys Asn Asn Gly Arg Gly Ser Pro Leu Ala Phe Tyr His
            1155                1160                1165

Val Gln Asn Ile Ala Val Glu Ile Thr Glu Ser Phe Val Asp Tyr Ile
            1170                1175                1180

Lys Thr Lys Pro Ile Val Phe Glu Val Phe Gly His Tyr Gln Gln His
1185                1190                1195                1200

Pro Leu His Leu Gln Gly Gln Glu Leu Asn Ser Pro Gln Pro Cys
            1205                1210                1215

Arg Arg Phe Phe Pro Pro Met Pro Leu Ser Lys Pro Val Pro Ala
            1220                1225                1230

Thr Lys Leu Asn Thr Met Ser Lys Thr Ser Leu Gly Gln Ser Met Ser
            1235                1240                1245

Lys Tyr Asp Leu Leu Val Trp Phe Glu Ile Ser Glu Leu Glu Pro Thr
            1250                1255                1260

Gly Glu Tyr Ile Pro Ala Val Val Asp His Thr Ala Gly Leu Pro Cys
1265                1270                1275                1280

Gln Gly Thr Phe Leu Leu His Gln Gly Ile Gln Arg Arg Ile Thr Val
            1285                1290                1295

Thr Ile Ile His Glu Lys Gly Ser Glu Leu His Trp Lys Asp Val Arg
            1300                1305                1310

Glu Leu Val Val Gly Arg Ile Arg Asn Lys Pro Glu Val Asp Glu Ala
            1315                1320                1325

Ala Val Asp Ala Ile Leu Ser Leu Asn Ile Ile Ser Ala Lys Tyr Leu
            1330                1335                1340

Lys Ser Ser His Asn Ser Ser Arg Thr Phe Tyr Arg Phe Glu Ala Val
1345                1350                1355                1360

Trp Asp Ser Ser Leu His Asn Ser Leu Leu Leu Asn Arg Val Thr Pro
            1365                1370                1375

Tyr Gly Glu Lys Ile Tyr Met Thr Leu Ser Ala Tyr Leu Glu Leu Asp
            1380                1385                1390

His Cys Ile Gln Pro Ala Val Ile Thr Lys Asp Val Cys Met Val Phe
            1395                1400                1405

Tyr Ser Arg Asp Ala Lys Ile Ser Pro Pro Arg Ser Leu Arg Ser Leu
            1410                1415                1420

Phe Gly Ser Gly Tyr Ser Lys Ser Pro Asp Ser Asn Arg Val Thr Gly
1425                1430                1435                1440

Ile Tyr Glu Leu Ser Leu Cys Lys Met Ser Asp Thr Gly Ser Pro Gly
            1445                1450                1455

Met Gln Arg Arg Arg Arg Lys Ile Leu Asp Thr Ser Val Ala Tyr Val
            1460                1465                1470

Arg Gly Glu Glu Asn Leu Ala Gly Trp Arg Pro Arg Gly Asp Ser Leu
            1475                1480                1485

Ile Leu Glu His Gln Trp Glu Leu Glu Lys Leu Glu Leu Leu His Glu
            1490                1495                1500

Val Glu Lys Thr Arg His Phe Leu Leu Arg Glu Arg Leu Gly Asp
1505                1510                1515                1520

Ser Ile Pro Lys Ser Leu Ser Asp Ser Leu Ser Pro Ser Leu Ser Ser
            1525                1530                1535

Gly Thr Leu Ser Thr Ser Thr Ser Ile Ser Ser Gln Ile Ser Thr Thr
```

-continued

```
            1540              1545              1550
Thr Phe Glu Ser Ala Ile Thr Pro Ser Glu Ser Gly Tyr Asp Ser
     1555              1560              1565
Gly Asp Ile Glu Ser Leu Val Asp Arg Glu Lys Glu Leu Ala Thr Lys
     1570              1575              1580
Cys Leu Gln Leu Leu Thr His Thr Phe Asn Arg Glu Phe Ser Gln Val
1585              1590              1595              1600
His Gly Ser Val Ser Asp Cys Lys Leu Ser Asp Ile Ser Pro Ile Gly
              1605              1610              1615
Arg Asp Pro Ser Glu Ser Ser Phe Ser Ser Ala Thr Leu Thr Pro Ser
         1620              1625              1630
Ser Thr Cys Pro Ser Leu Val Asp Ser Arg Ser Asn Ser Leu Asp Gln
    1635              1640              1645
Lys Thr Pro Glu Ala Asn Ser Arg Ala Ser Ser Pro Cys Pro Glu Phe
    1650              1655              1660
Glu Gln Phe Gln Ile Val Pro Ala Val Glu Thr Pro Tyr Leu Ala Arg
1665              1670              1675              1680
Ala Gly Lys Asn Glu Phe Leu Asn Leu Val Pro Asp Ile Glu Glu Ile
              1685              1690              1695
Arg Pro Ser Ser Val Val Ser Lys Lys Gly Tyr Leu His Phe Lys Glu
         1700              1705              1710
Pro Leu Tyr Ser Asn Trp Ala Lys His Phe Val Val Arg Arg Pro
    1715              1720              1725
Tyr Val Phe Ile Tyr Asn Ser Asp Lys Asp Pro Val Glu Arg Gly Ile
    1730              1735              1740
Ile Asn Leu Ser Thr Ala Gln Val Glu Tyr Ser Glu Asp Gln Gln Ala
1745              1750              1755              1760
Met Val Lys Thr Pro Asn Thr Phe Ala Val Cys Thr Lys His Arg Gly
              1765              1770              1775
Val Leu Leu Gln Ala Leu Asn Asp Lys Asp Met Asn Asp Trp Leu Tyr
         1780              1785              1790
Ala Phe Asn Pro Leu Leu Ala Gly Thr Ile Arg Pro Gly His Leu Ala
    1795              1800              1805
Ser Glu Ile Ile Arg Glu Asp Lys Ser Val Ser Phe Ser Cys Gln
    1810              1815              1820

<210> SEQ ID NO 3
<211> LENGTH: 4146
<212> TYPE: DNA
<213> ORGANISM: Homo sapiens

<400> SEQUENCE: 3 atgggtccc tcacttcatc cccatcttcc tgctcactca gtagtcaggt gggcttgacg      60
tctgtgacca gtattcaaga gaggatcatg tctacacctg aggagaggag agctattgaa     120
cgtttaaagg aatcagagaa gatcattgct gagttgaatg aaacttggga agagaagctt     180
cgtaaaacag aggccatcag aatggagaga gaggctttgt tggctgagat gggagttgcc     240
attcgggaag atggaggaac cctaggggtt ttctcaccta aaaagacccc acatcttgtt     300
aacctcaatg aagacccact aatgtctgag tgcctacttt attacatcaa agatggaatt     360
acaagggttg gccaagcaga tgctgagcgg cgccaggaca tagtgctgag cggggctcac     420 attaagaag agcattgtat cttccggagt gagagaagca acagcgggga agttatcgtg     480
accttagagc cctgtgagcg ctcagaaacc tacgtaaatg caagagggt gtcccagcct     540
```

| | |
|---|---|
| gttcagctgc gctcaggaaa ccgtatcatc atgggtaaaa accatgttt ccgctttaac | 600 |
| cacccggaac aagcacgagc tgagcgagag aagactcctt ctgctgagac cccctctgag | 660 |
| cctgtggact ggacatttgc ccagagggag cttctggaaa acaaggaat tgatatgaaa | 720 |
| caagagatgg agaaaaggct acaggaaatg agatcttat acaaaagga gaaggaagaa | 780 |
| gcagatcttc ttttggagca gcagagactg gactatgaga gtaaattgca ggccttgcag | 840 |
| aagcaggttg aaacccgatc tctggctgca gaaacaactg aagaggagga agaagaggaa | 900 |
| gaagttcctt ggacacagca tgaatttgag ttggcccaat gggccttccg gaaatggaag | 960 |
| tctcatcagt ttacttcatt acgggactta ctctggggca atgccgtgta cctaaaggag | 1020 |
| gccaatgcca tcagtgtgga actgaaaaag aaggtgcagt ttcagtttgt tctgctgact | 1080 |
| gacacactgt actccccttt gcctcctgaa ttacttccca ctgagatgga aaaaactcat | 1140 |
| gaggacaggc ctttccctcg cacagtggta gcagtagaag tccaggattt gaagaatgga | 1200 |
| gcaacacact attggtcttt ggagaaactc aagcagaggc tggatttgat gcagagatg | 1260 |
| tatgatagg caggggagat ggcctccagt gcccaagacg aaagcgaaac cactgtgact | 1320 |
| ggcagcgatc ccttctatga tcggttccac tggttcaaac ttgtggggag ctcccccatt | 1380 |
| ttccacggct gtgtgaacga gcgccttgcc gaccgcacac cctcccccac tttttccacg | 1440 |
| gccgattccg acatcactga gctggctgac gagcagcaag atgagatgga ggattttgat | 1500 |
| gatgaggcat tcgtggatga cgccggctct gacgcaggga cggaggaggg atcagatctc | 1560 |
| ttcagtgacg ggcatgaccc gttttacgac cgatcccctt ggttcatttt agtgggaagg | 1620 |
| gcatttgttt acctgagcaa tctgctgtat cccgtgcccc tgatccacag ggtggccatc | 1680 |
| gtcagtgaga aggtgaagt gcggggattt ctgcgtgtgg ctgtacaggc catcgcagcg | 1740 |
| gatgaagaag ctcctgatta tggctctgga attcgacagt caggaacagc taaaatatct | 1800 |
| tttgataatg aatactttaa tcagagtgac ttttcgtctg ttgcaatgac tcgttctggt | 1860 |
| ctgtccttgg aggagttgag gattgtggaa ggacagggtc agagttctga ggtcatcact | 1920 |
| cctccagaag aaatcagtcg aattaatgac ttggatttga agtcaagcac tttgctggat | 1980 |
| ggtaagatgg taatggaagg gttttctgaa gagattggca accacctgaa actgggcagt | 2040 |
| gccttcactt tccgagtaac agtgttgcag gccagtggaa tcctcccaga gtatgcagat | 2100 |
| atcttctgtc agttcaactt tttgcatcgc catgatgaag cattctccac ggagcccctc | 2160 |
| aaaaacaatg gcagaggaag tccctggcc ttttatcatg tgcagaatat tgcagtggag | 2220 |
| atcactgaat catttgtgga ttacatcaaa accaagccta ttgtatttga agtctttggg | 2280 |
| cattatcagc agcacccact tcatctgcaa ggacaggagc ttaacagtcc gcctcagccg | 2340 |
| tgccgccgat tcttccctcc acccatgcca ctgtccaagc cagttccagc caccaagtta | 2400 |
| aacacgatga gcaaaaccag ccttggccag agcatgagca gtatgaccct cctggtttgg | 2460 |
| tttgagatca gtgaactgga gcctacagga gagtatatcc cagctgtggt tgaccacaca | 2520 |
| gcaggcttgc cttgccaggg gacattttg cttcatcagg gcatccagcg aaggatcaca | 2580 |
| gtgaccatta tccatgagaa ggggagcgag ctccattgga agatgttcg tgaactggtg | 2640 |
| gtaggtcgta ttcggaataa gcctgaggtg gatgaagctg cagttgatgc catcctctcc | 2700 |
| ctaaatatta tttctgccaa gtacctgaag tcttcccaca actctagcag gaccttctac | 2760 |
| cgctttgagg ctgtgtggga tagctctctg cataactccc ttcttctgaa ccgagtgaca | 2820 |
| ccctatggag aaaaagatcta catgaccttg tcggcctacc tagagctgga tcattgcatc | 2880 |
| cagccggctg tcatcaccaa ggatgtgtgc atggtcttct actcccgaga tgccaagatc | 2940 |

-continued

```
tcaccaccac gctctctgcg tagcctctttt ggcagcggct actcaaagtc accagattcg    3000
aatcgagtca ctggcattta cgaactcagc ttatgcaaaa tgtcagacac aggtagtcca    3060
ggtatgcaga gaaggagaag aaaaatctta gatacgtcag tggcatatgt gcggggagaa    3120
gagaacttag caggctggcg gccccgtgga gacagcctca tccttgagca ccagtgggag    3180
ctggagaagc tggagctcct acatgaggtg aaaaaaccc gccactttt gctgctgcgt      3240 gagagacttg gtgacagcat ccccaaatcc ctgagcgact cgttatcccc cagcctcagc    3300
agtgggaccc tcagcacctc caccagtatc tcctctcaga tctcaaccac taccttgaa    3360 agcgccatca cacctagcga gagcagtggc tatgattcag gagacatcga aagcctggtg    3420
gaccgagaga aagagctggc taccaagtgc ctgcaacttc tcacccacac tttcaacaga    3480
gaattcagcc aggtgcacgg cagcgtcagt gactgtaagt tgtctgatat ctctccaatt    3540
ggacgggatc cctctgagtc cagtttcagc agtgccaccc tcactccctc ctccacctgt    3600
ccctctctgg tagactctag gagcaactct ctggatcaga agaccccaga agccaattcc    3660
cgggcctcta gtccctgccc agaatttgaa cagtttcaga ttgtcccagc tgtggaaaca    3720
ccatatttgg cccgagcagg aaaaaacgaa tttctcaatc ttgttccaga tattgaagaa    3780
attagaccaa gctcagtggt ctctaagaaa ggataccttc atttcaagga gcctctttac    3840
agtaactggg ctaaacattt tgttgtcgtc cgtcggcctt atgtcttcat ctataacagt    3900
gacaaagacc ctgtggagcg tggaatcatt aacctgtcca cagcacaggt ggagtacagt    3960
gaggaccagc aggccatggt gaagacacca acaccttttg ctgtctgcac aaagcaccgt    4020
ggggtccttt tgcaggccct caatgacaaa gacatgaacg actggttgta tgccttcaac    4080
ccacttctag ctggcacaat acggtcaaag ctttcccgca gatgcccgag ccagtcgaaa    4140
tactaa                                                                4146
```

<210> SEQ ID NO 4
<211> LENGTH: 5472
<212> TYPE: DNA
<213> ORGANISM: Homo sapiens

<400> SEQUENCE: 4

```
atgtcgggag cctcagtgaa ggtggctgtc cgggtaaggc ccttcaattc tcgagagacc      60
agcaaggaat ccaaatgcat cattcagatg caaggcaact cgaccagtat tattaaccca    120
aagaatccaa aggaagctcc aaagtccttc agcttcgact attcctactg gtctcatacc    180
tcacccgaag atccctgttt tgcatctcaa aaccgtgtgt acaatgacat tggcaaggaa    240
atgctcttac acgcctttga gggatataat gtctgtattt ttgcctatgg gcagactggt    300
gctggaaaat cttatacaat gatgggtaaa caagaagaaa gccaggctgg catcattcca    360
cagttatgtg aagaactttt tgagaaaatc aatgacaact gtaatgaaga atgtcttac    420 tctgtagagg tgagctacat ggaaatttac tgtgaaagag tacgagattt gctgaatcca    480
aaaaacaagg gtaatttgcg tgtgcgtgaa caccccacttc ttggacccta tgtggaggat    540
ctgtccaagt tggcagttac ttcctacaca gacattgctg acctcatgga tgctgggaac    600
aaagccagga cagtggcagc tacaaacatg aatgaaacaa gtagccgttc ccacgctgtg    660
tttacgattg ttttcaccca agagaaacac gataatgaga ccaacctttc cactgagaag    720
gtcagtaaaa tcagcttggt ggatctagca ggaagtgaac gagctgattc aactggtgcc    780
aaagggactc gattaaagga aggagcaaat attaataagt ctcttacaac tttgggcaaa    840
```

| | |
|---|---|
| gtcatttcag ccttggccga ggtggataac tgcactagca agagtaaaaa gaagaagaaa | 900 |
| acagatttta ttccctacag ggattctgta cttacttggc tccttcgaga aaatttaggt | 960 |
| ggcaattctc ggactgcaat ggttgctgct ctgagccccg cggatatcaa ctacgatgag | 1020 |
| actttgagca ctctgagata tgcagatcgt gcaaaacaaa ttaaatgcaa tgctgttatc | 1080 |
| aatgagggcc ccaatgccaa gctggttcgt gaattaaagg aggaggtgac acggctgaag | 1140 |
| gaccttcttc gtgctcaggg cctggagat attattgata ttgatccact gatcgatgat | 1200 |
| tactctggaa gtggaagcaa atatctgaaa gattttcaga acaataagca tagatacttg | 1260 |
| ctagcctctg agaatcaacg ccctggccat ttttccacag catccatggg gtccctcact | 1320 |
| tcatccccat cttcctgctc actcagtagt caggtgggct tgacgtctgt gaccagtatt | 1380 |
| caagagagga tcatgtctac acctggagga aggaagcta ttgaacgttt aaaggaatca | 1440 |
| gagaagatca ttgctgagtt gaatgaaact tgggaagaga agcttcgtaa aacagaggcc | 1500 |
| atcagaatgg agagagaggc tttgttggct gagatgggga ttgccattcg ggaagatgga | 1560 |
| ggaaccctag gggttttctc acctaaaaag accccacatc ttgttaaccct caatgaagac | 1620 |
| ccactaatgt ctgagtgcct actttattac atcaaagatg gaattacaag ggttggccaa | 1680 |
| gcagatgctg agcggcgcca ggacatagtg ctgagcgggg ctcacattaa agaagagcat | 1740 |
| tgtatcttcc ggagtgagag aagcaacagc ggggaagtta tcgtgacctt agagccctgt | 1800 |
| gagcgctcag aaacctacgt aaatggcaag agggtgtccc aacctgttca gctgcgctca | 1860 |
| ggaaaccgta tcatcatggg taaaaaccat gttttccgct ttaaccaccc ggaacaagca | 1920 |
| cgagctgagc gagagaagac tccttctgct gagaccccct ctgagcctgt ggactggaca | 1980 |
| tttgcccaga gggagcttct ggaaaaacaa ggaattgata tgaaacaaga gatggagaaa | 2040 |
| aggctacagg aaatggagat cttatacaaa aaggagaagg aagaagcaga tcttcttttg | 2100 |
| gagcagcaga gactggacta tgagagtaaa ttgcaggcct tgcagaagca ggttgaaacc | 2160 |
| cgatctctgg ctgcagaaac aactgaagag gaggaagaag aagaagaagt tccttggaca | 2220 |
| cagcatgaat ttgagttggc ccaatgggcc ttccggaaat ggaagtctca tcagtttact | 2280 |
| tcattacggg acttactctg gggcaatgcc gtgtacctaa aggaggccaa tgccatcagt | 2340 |
| gtggaactga aaagaaggt gcagtttcag tttgttctgc tgactgacac actgtactcc | 2400 |
| cctttgcctc ctgaattact tcccactgag atggaaaaaa ctcatgagga caggcctttc | 2460 |
| cctcgcacag tggtagcagt agaagtccag gatttgaaga atggagcaac acactattgg | 2520 |
| tctttggaga aactcaagca gaggctggat ttgatgcgag agatgtatga tagggcaggg | 2580 |
| gagatggcct ccagtgccca agacgaaagc gaaaccactg tgactggcag cgatcccttc | 2640 |
| tatgatcggt tccactggtt caaacttgtg gggagctccc ccattttcca cggctgtgtg | 2700 |
| aacgagcgcc ttgccgaccg cacaccctcc cccactttt ccacggccga ttccgacatc | 2760 |
| actgagctgc tgacgagca gcaagatgag atggaggatt tgatgatga ggcattcgtg | 2820 |
| gatgacgccg gctctgacgc agggacggag gagggatcag atctcttcag tgacgggcat | 2880 |
| gacccgtttt acgaccgatc cccttggttc attttagtgg gaagggcatt tgtttacctg | 2940 |
| agcaatctgc tgtatcccgt gcccctgatc cacagggtgg ccatcgtcag tgagaaaggt | 3000 |
| gaagtgcggg gatttctgcg tgtggctgta caggccatcg cagcggatga agaagctcct | 3060 |
| gattatggct ctggaattcg acagtcagga acagctaaaa tatctttga taatgaatac | 3120 |
| tttaatcaga gtgactttc gtctgttgca atgactcgtt ctggtctgtc cttggaggag | 3180 |
| ttgaggattg tggaaggaca gggtcagagt tctgaggtca tcactcctcc agaagaaatc | 3240 |

```
agtcgaatta atgacttgga tttgaagtca agcactttgc tggatggtaa gatggtaatg    3300
gaagggtttt ctgaagagat tggcaaccac ctgaaactgg gcagtgcctt cactttccga    3360
gtaacagtgt tgcaggccag tggaatcctc ccagagtatg cagatatctt ctgtcagttc    3420 aacttttttgc atcgccatga tgaagcattc tccacggagc cctcaaaaa caatggcaga    3480 ggaagtcccc tggccttttta tcatgtgcag aatattgcag tggagatcac tgaatcattt    3540
gtggattaca tcaaaaccaa gcctattgta tttgaagtct ttgggcatta tcagcagcac    3600
ccacttcatc tgcaaggaca ggagcttaac agtccgcctc agccgtgccg ccgattcttc    3660
cctccaccca tgccactgtc caagccagtt ccagccacca agttaaacac gatgagcaaa    3720
accagccttg ccagagcat gagcaagtat gacctcctgg tttggtttga gatcagtgaa    3780
ctggagccta caggagagta tatcccagct gtggttgacc acacagcagg cttgccttgc    3840 cagggggacat ttttgcttca tcagggcatc cagcgaagga tcacagtgac cattatccat    3900
gagaagggga gcgagctcca ttggaaagat gttcgtgaac tggtggtagg tcgtattcgg    3960
aataagcctg aggtggatga agctgcagtt gatgccatcc tctccctaaa tattatttct    4020
gccaagtacc tgaagtcttc ccacaactct agcaggacct tctaccgctt tgaggctgtg    4080
tgggatagct ctctgcataa ctcccttctt ctgaaccgag tgacaccta tggagaaaag    4140 atctacatga ccttgtcggc ctaccttagag ctggatcatt gcatccagcc ggctgtcatc    4200
accaaggatg tgtgcatggt cttctactcc cgagatgcca agatctcacc accacgctct    4260
ctgcgtagcc tctttggcag cggctactca aagtcaccag attcgaatcg agtcactggc    4320
atttacgaac tcagcttatg caaaatgtca gacacaggta gtccaggtat gcagagaagg    4380
agaagaaaaa tcttagatac gtcagtggca tatgtgcggg gagaagagaa cttagcaggc    4440
tggcggcccc gtggagacag cctcatcctt gagcaccagt gggagctgga gaagctggag    4500
ctcctacatg aggtggaaaa aacccgccac tttttgctgc tgcgtgagag acttggtgac    4560
agcatcccca aatccctgag cgactcgtta tcccccagcc tcagcagtgg gaccctcagc    4620
acctccacca gtatctcctc tcagatctca accactacct tgaaaagcgc catcacacct    4680
agcgagagca gtggctatga ttcaggagac atcgaaagcc tggtggaccg agagaaagag    4740
ctggctacca agtgcctgca acttctcacc cacactttca acagagaatt cagccaggtg    4800
cacggcagcg tcagtgactg taagttgtct gatatctctc caattggacg ggatccctct    4860
gagtccagtt tcagcagtgc caccctcact ccctcctcca cctgtccctc tctggtagac    4920
tctaggagca actctctgga tcagaagacc ccagaagcca attcccgggc ctctagtccc    4980
tgcccagaat ttgaacagtt tcagattgtc ccagctgtgg aaacaccata tttggcccga    5040
gcaggaaaaa acgaatttct caatcttgtt ccagatattg aagaaattag accaagctca    5100
gtggtctcta agaaaggata ccttcatttc aaggagcctc tttacagtaa ctgggctaaa    5160 catttttgttg tcgtccgtcg gccttatgtc ttcatctata acagtgacaa agaccctgtg    5220
gagcgtggaa tcattaacct gtccacagca caggtggagt acagtgagga ccagcaggcc    5280
atggtgaaga caccaaacac ctttgctgtc tgcacaaagc accgtggggt cctttttgcag    5340 gccctcaatg acaaagacat gaacgactgg ttgtatgcct tcaacccact tctagctggc    5400
acaatacgac caggtcatct ggcttccgag atcatcagag aagataagtc tgtctctttc    5460
agctgccagt aa                                                        5472
```

<210> SEQ ID NO 5

```
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 5
ctattggtct ttggagaaac                                                20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 6
tacagccaca cgcagaaatc                                                20

<210> SEQ ID NO 7
<211> LENGTH: 302
<212> TYPE: DNA
<213> ORGANISM: Artificial Sequence
<220> FEATURE:
<223> OTHER INFORMATION: Description of Artificial Sequence: Synthetic
      antisense nucleotide sequence

<400> SEQUENCE: 7
gacattggca aggaaatgct cttacacgcc tttgagggat ataatgtctg tattttgcc     60 tatgggcaga ctggtgctgg aaaatcttat acaatgatgg gtaaacaaga agaaagccag   120
gctggcatca ttccacagtt atgtgaagaa cttttttgaga aaatcaatga caactgtaat 180
gaagaaatgt cttactctgt agaggtgagc tacatggaaa tttactgtga aagagtacga  240
gatttgctga atccaaaaaa caagggtaat ttgcgtgtgc gtgaacaccc acttcttgga  300
cc                                                                  302
```

NUCLEIC ACID OF NOVEL HUMAN KINESIN-RELATED GENE PROTEIN ENCODED BY THE NUCLEIC ACID PEPTIDE FRAGMENT THEREOF AND ANTICANCER AGENTS COMPRISING THE NUCLEIC ACID AND THE LIKE

CROSS-REFERENCED APPLICATION

This application is a National phase of International Application PCT/JP01/08635, filed Oct. 1, 2001, which designated the U.S. and that International Application was not published under PCT Article 21(2) in English.

1. Technical Field

This invention relates to novel human kinesin-related genes, to information on proteins encoded by the genes, and to their application for the treatment of or for diagnosing prognosis of cancer.

2. Background Art

Substance Transport in Neurons

Different substances are transported in neuronal axons by specific systems, and such transport is classified as two types, either "fast transport" or "slow transport", depending on the speed. "Fast transport" includes both anterograde transport in the direction from the cell body to the axon terminal, and retrograde transport in the opposite direction. "Fast transport" is oriented movement, generally inside the cell, and it is produced by the motion of intracellular organelle-attached molecular motors (motor proteins) on microtubules.

Role of Kinesin in Axonal Transport

Kinesin carries intracellular organelles in the plus end direction of microtubules, accomplishing fast anterograde transport in the neuronal axon. The kinesin molecule is a heterotetramer comprised of two 120 kDa heavy chains and two 64 kDa light chains. The N-terminal end of the heavy chain forms a globular head constituting a motor domain which binds with ATP and microtubules, and extends to form a rod-shaped stalk and fan-shaped tail, with a total length of approximately 80 nm (Hirokawa N. et al., Cell 56:867–878, (1989)). The light chain may be any of 3 molecular species, produced by splicing (Cyr J L. et al., Proc. Natl. Acad. Sci. USA 88:10114–10118, (1991)), and differ depending on the particular organ. The light chain attaches to the tail of the heavy chain, and binding to membrane organelles occurs at the heavy chain tail/light chain portions.

Kinesin-related Genes

Several kinesin-related genes have recently been discovered, and their protein structures elucidated. These kinesin-related genes have highly conserved motor domain structures (Eyer J. et al., Nature 391:584–587 (1998)). Over 30 different kinesin-related proteins have been discovered in mice to date, all having motor structures (Gibbons I R. et al., Cell Motil. Cytoskel. 32:136–144 (1995)), and they are collectively known as the kinesin superfamily. A phylogenetic tree of the kinesin superfamily has recently been published (Hirokawa N. et al., Science 279:519–526 (1998)), and several of the members have been found to be involved in axonal transport.

The kinesin superfamily is being actively researched in mice, where it is designated as KIF (Aizawa H. et al., J. Cell Biol. 119:1287–1296 (1992)), and the members are largely divided into three groups based on the position of the motor domain (at the N-terminal end, at the central part or at the C-terminal end).

N-terminal Motor Kinesin Superfamily

The N-terminal motor kinesin superfamily is further divided into the KHC, Unc104, RP85/95, BimC, MKLP1 and chromokinesin subfamilies. Among these, the BimC family has not been identified in mammals.

The KHC family includes three members identified in mice (KIF5B, KIF5A, KIF5C) and two in humans (HsuKHC, HsnKHC), while only one has been identified in invertebrates. This family can be divided into the ubiquitous members (KIF5B, HsuKHC) and nerve system-specific members (KIF5A, KIF5C, HsnKHC). HsnKHC is distributed throughout the nerve cell body and HsuKHC is found in the axon as well (Niclas J. et al., Neuron 12:1059–1072 (1994)).

The Unc104 family has not been identified in humans, but KIF1A and KIF1B are known in mice. KIF1A is a large 1695 amino acid, 200 kDa protein which works with a single head and carries synaptic vesicle precursors toward the plus microtubule end at a speed of 1.2–1.5 µm/s (Okada Y. et al., Cell 81:769–780 (1995)). Gene targeting results in serious kinesthetic impairment, and leads to death shortly after birth.

KIF1B is comprised of 1150 amino acids and also works with a single head, carrying mitochondria toward the plus microtubule end at a speed of 0.5 µm/s (Nangaku M. et al., Cell 79:1209–1220 (1994)).

Murine KIF3A and KIF3B of the RP85/95 family exist as a two-headed heterodimer, and form a heterotrimer in association with KAP3. These kinesin-related proteins are non-neuron-specific and carry membrane vesicles, which are larger than synapse vesicles, toward the microtubule plus end at a speed of 0.3 µm/s (Yamazaki H. et al., Proc. Natl. Acad. Sci. USA 93:8443–8448 (1996)).

One member of the MKLP family is known in humans (human MKLP). Human MKLP1 carries out functions for spindle elongation in anaphase B, formation of contractile rings and completion of cytoplasmic division.

Murine KIF4 of the chromokinesin family is comprised of 1231 amino acids, and has a length of 116 nm with two heads. It moves at a speed of 0.2 µm/s, transporting membrane vesicles to growth cones. In the adult body it is most abundant in the immune system organs (Shingyoji C. et al., Nature 393:711–714 (1998)).

Central Motor Kinesin Superfamily

The central motor kinesin superfamily has not been identified in humans. Murine KIF2 is a two-headed 81 kDA protein which moves toward the microtubule plus end at a speed of 0.4 µm/s. This kinesin-related protein is non-neuron-specific, but is expressed in the juvenile nerve system where it carries out transport of membrane vesicles to growth cones (Noda Y. et al., J. Cell Biol. 129:157–167 (1995)).

C-terminal Motor Kinesin Superfamily

The C-terminal motor kinesin superfamily has also not been identified in humans. Three different murine kinesins are known in this superfamily (KIFC1, KIFC2, KIFC3). KIFC2 is absent in the peripheral nerves, abundant in dendrites, and mainly carries multivesicular bodies toward the ends of dendrites (Saito N. et al., Neuron 18:425–438 (1997)).

Cloning of Novel Human Kinesin-related Gene Fragments cDNA for KIAA0591 (GenBank® brand computerized storage and retrieval services dealing with information relating to nucleic acid sequence data, accession number:

AB011163) has been cloned from a molecular weight fractionated human brain cDNA library (Nagase T. et al., DNA Res. 5:31–39 (1998)).

The cDNA consisted of 5368 bases and is a partial fragment of a novel gene which is highly homologous to the synapse vesicle transporter gene in human neuronal axons. Since the 5' end of the KIAA0591 cDNA lacked the transcription initiation codon and was shorter than the corresponding approximately 9.5 kb transcription product, this suggested the existence of longer full-length cDNA.

The present inventors, therefore, screened a human substantia nigra cDNA library in order to obtain the full-length cDNA including KIAA0591, but without succeeding in elucidating the full-length cDNA; and its function hence remains unknown.

However, in the course of attempting to elucidate the full-length cDNA for KIAA0591, the present inventors also discovered a kinesin-related gene with no portion corresponding to the motor domain seen ubiquitously in the kinesin superfamily. The base sequence for the translation region of this gene is set forth in SEQ ID NO: 3 in the Sequence Listing, and the protein translated from this region is set forth in SEQ ID NO: 1, respectively.

It was also discovered that the gene is located at 36.2–36.3 on the small arm of human chromosome 1, which has been found to be often deficient in neuroblastomas and the like, that no mutations are found in the region encoding this gene in 8 types of neuroblastoma and 15 types of neuroblastoma-derived cell lines, and that it is expressed in a wide range of adult tissues and strongly expressed in the brain, kidney, skeletal muscle and pancrea, particularly in the brain of a human fetus (Nakagawara A. et al., International Journal of Oncology 16:907–916 (2000)).

Nevertheless, the function of the motor domain-lacking kinesin related gene and its protein had remained unclear.

Anchorage-independent Growth and Cancer

Normal adherent cells require adhesion to a firm anchor in order to proliferate. When cultured on a non-adherable substance surface, the cells will survive for an extended period but will not proliferate. For example, when normal cells are suspended in a non-anchoring semi-solid medium such as agarose gel, life-supporting metabolism is carried out but growth is suppressed. On the other hand, malignantly transformed cells such as cancer cells (or oncocytes) generally lack the requirement for adhesion, and thus form colonies and grow even when suspended in non-anchoring semi-solid medium. This characteristic is very strongly implicated in the tumor-forming ability of malignantly transformed cells. Specifically, cells that proliferate in an anchorage-independent manner are efficient at forming tumors when injected into animals (See Darnell et al., Molecular Cell Biology, Second Edition 24:963–967 (1993)).

Cell Adhesion and Cancer Infiltration/Metastasis

Cancer is malignant because of its ability to infiltrate and metastasize. While research toward elucidating the mechanism has been actively pursued to date, infiltration and metastasis are complex phenomena that occur as a result of conflict between cancer cells and host cells, and the complete picture is not yet fully understood. Hematogenous metastasis is established by infiltration of cancer cells from primary lesions, intravasation, transport, colonization, extravasation and initial stage growth. Lymphogenous metastasis, disseminated metastasis and intracanalicular metastasis are also thought to involve similar processes. Adhesion and dissociation between cancer cell/cancer cell, cancer cell/normal cell and cancer cell/extracellular matrix occur throughout all of these processes.

Because reduced adhesion between cancer cells is seen in many types of cancer, there has been a focus on its connection with the cells' capability of infiltration and metastasis. Cancer cells contact many and various normal cells during the course of their metastasis. The cancer cells adhering to endothelial cells include those encapsulated by endothelial cells, those that adhere to the endothelial cell apical surface and those that are covered by the epithelial cell basal surface, and these are closely connected with intravasation and extravasation of the cancer cells. Adhesion between cancer cells and the extracellular matrix is also ubiquitously observed. Other observations have suggested cell fusion and death of normal cells occurring after adhesion of cancer cells to normal cells (Turuo, T. et al.: "Ganten'i no Bunshikiko" [Molecular Mechanisms of Cancer Metastasis], Medical View Publishing (1993)).

As stated above, the function of the novel motor domain-lacking kinesin-related gene and its encoded protein previously discovered by the present inventors had remained unknown. In addition, despite prediction of the existence of the full-length cDNA including KIAA0591, it had not yet been confirmed or identified.

DISCLOSURE OF THE INVENTION

This invention has been accomplished in light of the circumstances described above. An object of the invention is to provide base sequence data for a novel human kinesin-related gene having a motor domain. The invention further provides information relating to the function of the proteins encoded by the novel human kinesin-related gene with a motor domain and by the kinesin-related gene without a motor domain.

As a result of much diligent research, the present inventors have succeeded in cloning by Rapid Amplification of cDNA Ends (RACE) a novel gene having a longer 5' end than the kinesin-related gene without a motor domain (SEQ ID NO: 3), and in sequencing the full-length cDNA of this kinesin-related gene with a motor domain. For convenience, the novel kinesin-related gene with a motor domain has been designated as KIF1b-β, and its cDNA sequence (base sequence) is set forth in SEQ ID NO: 4 in the Sequence Listing.

The present inventors also discovered that expression of the KIF1b-β gene is enhanced only in neuroblastoma clinical tissue with favorable prognosis.

It was further discovered that suppressing expression of the KIF1b-β gene and the kinesin-related gene without a motor domain using antisense RNA allows anchorage-independent growth of normal cells which inherently grow only in an anchorage-dependent manner, or in other words, that these genes function to control canceration of normal cells.

The present inventors still further discovered that normal cells undergo tumorigenesis when expression of the KIF1b-β gene and the novel kinesin-related gene without a motor domain are suppressed using antisense RNA. Thus, loss of these genes facilitates tumorigenesis of normal cells.

In summary, this invention provides the nucleic acids and proteins or their pharmaceutically acceptable salts described in 1–12 below. The invention also provides the use of the nucleic acids and proteins or their pharmaceutically acceptable salts for treatment or diagnosis as described in 13–17 below.

1. A nucleic acid having the base sequence set forth in SEQ ID NO: 4 in the Sequence Listing.

2. A nucleic acid having a base sequence encoding a protein comprising the amino acid sequence set forth in SEQ ID NO: 2 in the Sequence Listing.

3. A nucleic acid which is a fragment of the nucleic acid according to 1. or 2. above.

4. A nucleic acid capable of hybridizing to the nucleic acid according to any one of 1. to 3. above.

5. A nucleic acid having the base sequence set forth in SEQ ID NO: 7 in the Sequence Listing.

6. An antisense nucleic acid to a nucleic acid according to 1. or 2. above.

7. An antisense nucleic acid having the base sequence set forth in SEQ ID NO: 7 in the Sequence Listing, characterized by promoting anchorage-independent growth of normal cells upon introduction into normal cells.

8. A protein having the amino acid sequence set forth in SEQ ID NO: 2 in the Sequence Listing, or a pharmaceutically acceptable salt thereof.

9. A protein having an amino acid sequence substantially identical to the amino acid sequence set forth in SEQ ID NO: 2 in the Sequence Listing and whose absence induces tumorigenesis of normal cells, or a pharmaceutically acceptable salt thereof.

10. The protein according to 9. above, characterized in that the amino acid sequence substantially identical to the amino acid sequence set forth in SEQ ID NO: 2 in the Sequence Listing is an amino acid sequence derivable by the substitution or the deletion of one or more amino acids in the amino acid sequence set forth in SEQ ID NO: 2 in the Sequence Listing, or by the addition of one or more amino acids to the amino acid sequence set forth in SEQ ID NO: 2 in the Sequence Listing, or a pharmaceutically acceptable salt thereof.

11. A protein having an the amino acid sequence derivable by the substitution or the deletion of one or more amino acids in the amino acid sequence set forth in SEQ ID NO: 1, or by the addition of one or more amino acids to the amino acid sequence set forth in SEQ ID NO: 1 and whose absence induces tumorigenesis of normal cells, or a pharmaceutically acceptable salt.

12. A partial peptide which is a functionally effective fragment of a protein having the amino acid sequence set forth in SEQ ID NO: 2 in the Sequence Listing, or a pharmaceutically acceptable salt thereof.

13. An anticancer agent comprising a protein having the amino acid sequence set forth in SEQ ID NO: 1 in the Sequence Listing, or a pharmaceutically acceptable salt thereof.

14. An anticancer agent comprising a protein having the amino acid sequence set forth in SEQ ID NO: 2 in the Sequence Listing, or a pharmaceutically acceptable salt thereof.

15. An anticancer agent comprising a nucleic acid having the base sequence set forth in SEQ ID NO: 3 in the Sequence Listing.

16. An anticancer agent comprising a nucleic acid having the base sequence set forth in SEQ ID NO: 4 in the Sequence Listing.

17. A method for diagnosing prognosis of human neuroblastoma, characterized by detecting the nucleic acid according to 1. above or a fragment thereof in a neuroblastoma clinical tissue sample.

18. A nucleic acid probe comprising the following nucleic acid (a) or (b):

(a) Nucleic acid having a portion of the base sequence set forth in SEQ ID NO: 4 in the Sequence Listing, or a base sequence complementary thereto;

(b) Nucleic acid which hybridizes to nucleic acid having the base sequence set forth in SEQ ID NO: 4 in the Sequence Listing under stringent conditions.

19. A primer comprising the following DNA (a) or (b):

(a) DNA having a portion of the base sequence set forth in SEQ ID NO: 4 in the Sequence Listing, or a base sequence complementary thereto;

(b) DNA which hybridizes to DNA having the base sequence set forth in SEQ ID NO: 4 in the Sequence Listing under stringent conditions.

20. A prognosis diagnosing kit for neuroblastoma comprising as an effective component thereof, the probe according to 18. above or the primer according to 19. above.

BEST MODE FOR CARRYING OUT THE INVENTION

Figure 1:
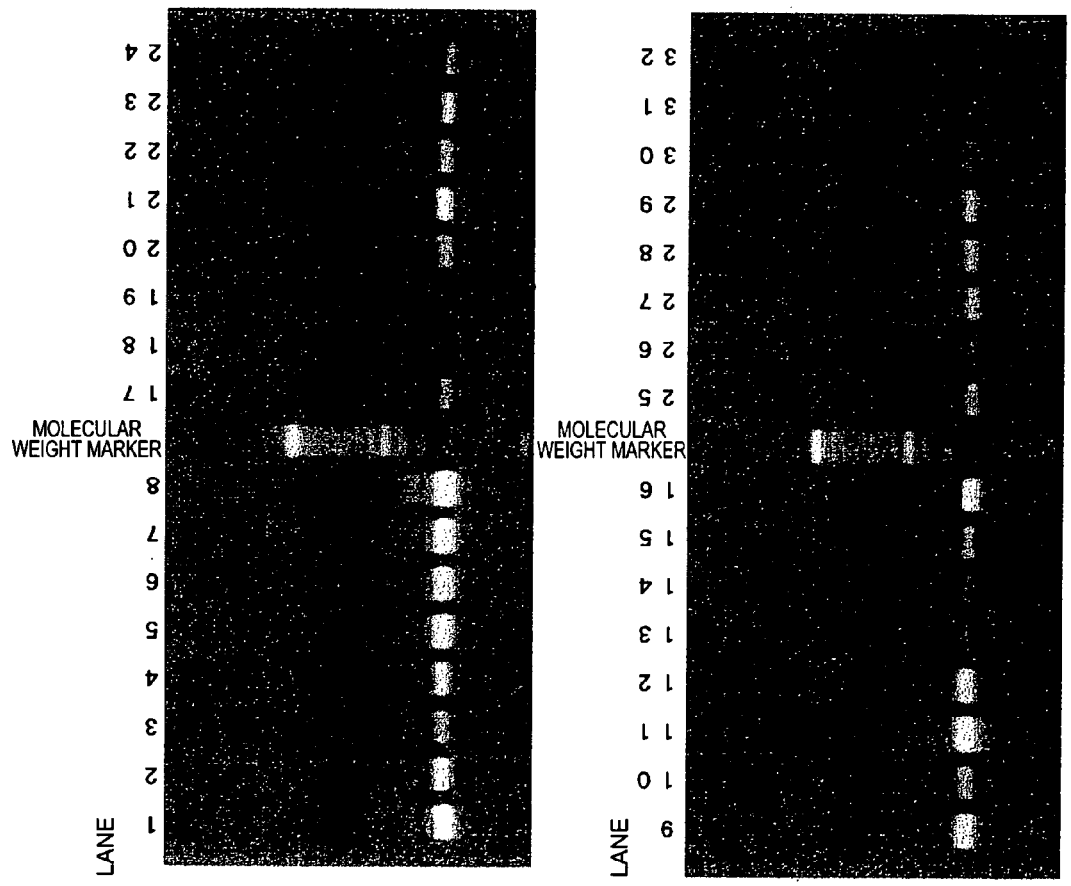
FIG. 1A and FIG. 1B are both representations corresponding to electrophoresis photographs showing the results of examining KIF1b-β gene expression in human neuroblastomas with favorable prognosis and with unfavorable prognosis, respectively, by semi-quantitative RT-PCR. In the figures, Lanes 1–16 represent clinical tissue samples of human neuroblastomas with favorable prognosis, and lanes 17–32 represent clinical tissue samples of human neuroblastomas with unfavorable prognosis.

The construction and preferred embodiments of the invention will now be described in detail.

The phrase, "protein having the amino acid sequence set forth in SEQ ID NO: 1" as used throughout the present specification may refer not only to a protein encoded by the nucleic acid set forth in SEQ ID NO: 3, but also to any protein with substantially equivalent activity. A protein with substantially equivalent activity is one having an amino acid sequence substantially identical to the amino acid. sequence set forth in SEQ ID NO: 1. The latter amino acid sequence may be, for example, an amino acid sequence derivable by the substitution or the deletion of one or more amino acids in the amino acid sequence set forth in SEQ ID NO: 1, or by the addition of one or more amino acids to the amino acid sequence set forth in SEQ ID NO: 1. Also, the phrase "protein having the amino acid sequence set forth in SEQ ID NO: 2" has an exactly corresponding meaning, and may refer not only to a protein encoded by the nucleic acid set forth in SEQ ID NO: 4, but also to any protein with substantially equivalent activity.

The phrase, "nucleic acid having the base sequence set forth in SEQ ID NO: 3" as used throughout the present specification may also refer to nucleic acid having a base sequence encoding a protein with substantially equivalent activity to the protein encoded by the nucleic acid set forth in SEQ ID NO: 3. The phrase "nucleic acid having the base sequence set forth in SEQ ID NO: 4" has an exactly corresponding meaning, and may also refer to nucleic acid having a base sequence encoding a protein with substantially equivalent activity to the protein encoded by the nucleic acid set forth in SEQ ID NO: 4. Such nucleic acids and protein variants may be prepared according to techniques known to one skilled in the art such as site-specific mutation, based on the base sequence information of the aforementioned nucleic acids.

The term "nucleic acid" as used throughout the present specification refers to DNA or RNA which encodes a protein as defined above or a partial peptide as a functionally effective fragment of the protein, which is complementary to a nucleic acid encoding such a protein or partial peptide, or which hybridizes to such nucleic acid under "stringent" conditions.

When the amount of expression of a nucleic acid of this invention is compared in neuroblastomas with favorable prognosis and with unfavorable prognosis, it is found to be expressed in greater amounts in neuroblastomas with favorable prognosis. Introducing antisense (nucleic acid) (described below) to the nucleic acid into normal cells promotes anchorage-independent growth of the normal cells and increases tumorigenesis. For these reasons, the nucleic acids of the invention are thought to have at least the function of maintaining biological normality (for example, suppressing cell canceration).

Thus, the nucleic acids of this invention (including their fragments), the proteins or partial peptides encoded by the nucleic acids (hereunder also referred to collectively as "proteins of the invention") and antisense for the nucleic acids may be used for diagnosis, treatment and prevention of the different diseases mentioned below (particularly malignant tumors).

(1) Usefulness for diagnosis

The nucleic acids, proteins and partial peptides of this invention, as well as antibodies for the proteins and partial peptides, are useful for diagnosis.

Specifically, these molecules may be used for detecting diseases (such as neuroblastoma) or disorders wherein increase or decrease in expression of the proteins of the invention or their partial peptides plays a role, by any of various assay methods, for the purpose of prognosis prediction, diagnosis and monitoring.

There are no particular limitations on methods of immunoassay using antibodies for the proteins of the invention or their partial peptides, and there may be mentioned various competitive and non-competitive assay methods using such techniques as Western blotting, radioimmunoassay, ELISA, "sandwich" immunoassay, immunoprecipitation, precipitin reaction, gel differentiation precipitation reaction, immunodiffusion assay, agglutination assay, complement-binding assay, immunoradiometric assay, fluorescent immunoassay and protein A immunoassay.

When using a nucleic acid of the invention for diagnosis, it may be used as a hybridization probe or as a PCR primer for detection of enhanced gene expression in cell specimens to identify prognosis. The enhanced gene expression can be examined by any method using as the probe a base sequence which hybridizes to any desired sequence among the base sequences disclosed by the invention. Preferably, a radioactive isotope-labeled probe is used for assay by Southern or Northern blotting. If the amount of nucleic acid hybridizing to the probe in the cell specimen is enhanced, diagnosis of favorable prognosis may be rendered. When the nucleic acid is used as a primer for PCR, RNA may be extracted from the specimen (cells) to be examined and the gene expression may be semi-quantitatively measured by RT-PCR.

(2) Usefulness for treatment

The nucleic acids, proteins and partial peptides of the invention are useful agents for treatment of diseases and disorders with which any of these are associated.

According to one embodiment of the invention, a pharmaceutical composition comprising a protein or partial peptide of the invention may be administered against a disease (particularly a malignant tumor) or disorder involving decreased expression of the protein or partial peptide. A pharmaceutical composition comprising the entirety or part of a nucleic acid of the invention may also be administered.

According to another embodiment, a pharmaceutical composition comprising antisense, neutralizing antibodies or a competitive inhibitor for a protein or partial peptide of the invention may be administered against a disease or disorder involving increased expression of the protein or peptide, to either suppress expression or inhibit the function of the protein or peptide.

Particularly when a nucleic acid of the invention is used for gene therapy for the purpose described above, the nucleic acid may be inserted into a vector used for gene transfer and the inserted gene may be expressed in the body of the patient under any desired expression promoter for treatment of cancer, for example.

The vector for insertion of the nucleic acid is preferably constructed based on a DNA or RNA virus. There are no particular limitations on the type of virus vector, and there may be used MoMLV vector, herpes virus vector, adenovirus vector, AAV vector, HIV vector, SIV vector, Sendai virus vector and the like.

There may be used, alternatively, a pseudotyped virus vector wherein one or more of the constitutive proteins of -the virus vector is replaced with a constitutive protein of a different type of virus, or wherein a portion of the nucleic acid sequence of the genetic information is replaced with a nucleic acid sequence of another type of virus. As an example there may be mentioned a pseudotyped virus vector wherein Env protein, the coat protein of HIV, is replaced with VSV-G protein, the coat protein of Vesicular Stomatitis Virus (VSV) (Naldini L. et al., Science 272:263–267 (1996)).

So long as the virus has a therapeutic effect, it may be used as a virus vector even if its host range is other than human. Non-virus-derived vectors may also be used, such as calcium phosphate/nucleic acid complexes, liposomes, cationic lipid complexes, Sendai virus liposomes, polymer carriers with polycationic backbone, and the like. The gene transfer system used may be electroporation, a gene gun, or the like.

An expression cassette including an expression promoter is preferred for gene expression of the nucleic acid of the invention inserted into the aforementioned vector.

The expression cassette used may be of any type which allows expression of the gene in target cells, with no particular limitations. One skilled in the art can easily select such an expression cassette, which is preferably an expression cassette allowing gene expression in animal-derived cells, more preferably an expression cassette allowing gene expression in mammalian cells and even more preferably an expression cassette allowing gene expression in human cells.

The expression cassette may include, in addition to the nucleic acid of the invention, various sequences such as a promoter or enhancer for the gene transcription, a polyA signal, a marker gene for labeling and/or selecting the gene-inserted cells, a viral gene sequence for efficient insertion of the gene into the genomic DNA sequence of the cell, and a signal sequence for extracellular secretion and/or local intracellular accumulation of the drug-acting substance produced by the gene expression.

For promoters sequences to be used in the expression cassette, there may be mentioned promoters derived from such viruses as adenovirus, cytomegalovirus, human immunodeficiency virus, simian virus 40, Rous sarcoma virus, herpes simplex virus, mouse leukemia virus, sindbis virus, hepatitis A virus, hepatitis B virus, hepatitis C virus, papillomavirus, human T cell leukemia virus, influenza virus, Japanese encephalitis virus, JC virus, parvovirus B19 and poliovirus, mammalian promoters such as albumin, SRα, heat shock protein and elongation factor promoters, chimeric promoters such as CAG promoter, and promoters whose activity is induced by tetracycline, steroids and the like.

(3) Pharmaceutical composition

The nucleic acids, proteins and partial peptides of this invention are used for treatment in the form of appropriate pharmaceutical compositions. The nucleic acids or the like are therefore prepared according to the formulation method described below, a preferred route of administration is established, and the dosage is determined so as to achieve the desired therapeutic effect.

(Formulation method)

The pharmaceutical composition comprising a nucleic acid, protein or peptide according to the invention is not particularly limited, and a drug may be constructed by encapsulation in liposomes, fine particles or microcapsules, expression in recombinant cells, receptor-mediated ingestion, or as a retrovirus or a portion of another type of vector.

More specifically, a recombinant virus vector comprising a nucleic acid of the invention may be dissolved in an appropriate solvent such as water, physiological saline or an isotonized buffer solution to prepare a composition containing the nucleic acid of the invention. Alternatively, a protein or partial peptide of the invention may be dissolved in an appropriate solvent such as water, physiological saline or an isotonized buffer solution to prepare a composition containing the protein or partial peptide of the invention. Polyethylene glycol, glucose, various amino acids, collagen, albumin or the like may be added as protective materials for the preparation.

The pharmaceutical composition of the invention may be formulated in neutralized form or in the form of a pharmaceutically acceptable salt. Pharmaceutically acceptable salts include those formed with the free amino group of a protein or peptide, such as those derived from hydrochloric acid, phosphoric acid, acetic acid, oxalic acid, tartaric acid or the like, and those formed with the free carboxyl group of a protein or peptide, such as those derived from sodium, potassium, ammonium, calcium, iron (II) hydroxide, isopropylamine, triethylamine, 2-ethylaminoethanol, histidine, procaine or the like.

(Administration method and dosage)

When a pharmaceutical composition of this invention is administered to the body, there are no particular limitations on the method of administration. It may be preferably carried out by injection intradermally, intramuscularly, intraperitoneally, intravenously, hypodermically or intranasally, for example. The dosage of the pharmaceutical composition of the invention will depend on the route of administration and the condition, age, body weight, sex, etc. of the administered patient, and the optimum dosage for a given patient may be determined by the practicing physician. In the case of injection, for example, the dosage is preferably about 0.1 µg/kg to 1000 mg/kg per day, and more preferably about 1 µg/kg to 100 mg/kg per day.

(4) Target diseases and disorders

There are no particular limitations on the target disease or disorder to be treated with a nucleic acid, protein or partial peptide of the invention as a drug, so long as the function of the nucleic acid, etc. is directly or indirectly associated with the condition. As mentioned above, introduction of antisense to the nucleic acid of the invention into normal cells promotes anchorage-independent growth of the normal cells and increases tumorigenesis. Accordingly, the nucleic acids, proteins and partial peptides of the invention clearly suppress normal cell canceration, and are particularly useful against malignant tumors.

There are no particular limitations on malignant tumors as targets of treatment by the nucleic acids, etc. of the invention, and there may be mentioned acute leukemia, chronic leukemia, lymphoma, fibrosarcoma, myxosarcoma, liposarcoma, hepatic cell carcinoma, choriocarcinoma, seminoma, embryonal carcinoma, Wilms tumor, bile duct carcinoma, testicular carcinoma, cervical carcinoma, lung carcinoma, small lung cell carcinoma, bladder carcinoma, epithelial carcinoma, glial cell carcinoma, medulloblastoma, epithelial cell carcinoma, angioblastoma, melanoma, neuroblastoma, retinoblastoma, chondrosarcoma, angiosarcoma, endothelial sarcoma, lymphangiosarcoma, colon carcinoma, breast carcinoma, ovarian carcinoma, prostate carcinoma, squamous cell carcinoma, adenocarcinoma, papillary carcinoma, papillar adenoma, cystadenocarcinoma and renal cell carcinoma. When the nucleic acids, etc. of the invention are used for treatment of malignant tumors, their function allows them to also be used as drugs to suppress metastasis of malignant tumors.

(5) Antisense (nucleic acid)

According to another embodiment of this invention, antisense nucleic acid is used which suppresses expression of a gene disclosed by the invention (including nucleic acids of the invention), to achieve a therapeutic or prophylactic effect. Here, "antisense nucleic acid" refers to a nucleic acid that can hybridize to a portion of RNA (preferably mRNA) of a gene of the invention due to a certain degree of sequence complementarity.

The antisense nucleic acid used may be in the form of a double-stranded or single-stranded, and either RNA or DNA (encoding the RNA) oligonucleotide, or a chimeric mixture thereof. The antisense nucleic acid is not particularly limited, and may consist of an oligonucleotide of preferably 5–500 and more preferably 200–500 bases. The oligonucleotide may also be modified in its base portion, ribose portion or phosphate backbone.

As a specific embodiment, the antisense nucleic acid may be used in the form of a catalytic RNA, ribozyme, or chimeric RNA-DNA analog.

The antisense nucleic acid may be synthesized by a method known to one skilled in the art using, for example, an automated DNA synthesizer.

When the antisense nucleic acid is used for the purpose of treatment or prevention, it may be administered to a patient as a pharmaceutical composition in the same manner described above for other nucleic acids, but most preferably, it is directly administered to specific cells (for example, cancer cells). Cells may also be transformed with a vector comprising DNA encoding RNA antisense nucleic acid, or transfected, to produce the antisense nucleic acid in the cells by transcription.

(6) Antibodies

According to yet another embodiment of the invention, antibodies against a protein or partial peptide of the invention, or fragments thereof including the binding domains, may be used as therapeutic or diagnostic agents. Specifically, for use as a therapeutic agent, an antibody may be bound to a specific region of a protein of the invention to act as an antagonist or agonist. For use as a diagnostic agent, antibodies may be used in various types of immunoassays for detection and measurement of a protein of the invention, as mentioned above.

The antibodies may be prepared using the protein or partial peptide of the invention, or its fragment, analog or derivative, as an immunogen according to methods known to one skilled in the art. For such antibodies, there may be mentioned polyclonal antibodies, monoclonal antibodies, chimeric antibodies, single-stranded antibodies, Fab fragments, or antibodies derived from an FAB expression library.

(7) Knockout animals

According to still another embodiment of the invention, there may be provided a nucleic acid sequence which knocks out expression of a gene of the invention, and knockout animals having that sequence inserted therein as a transgene. Cancer model animals may be constructed based on this information.

The invention will now be described in greater detail by way of examples; however, these examples are in no way limitative on the invention.

EXAMPLES

Example 1

Cloning of Full-length cDNA

Working from the amino acid sequence for the motor domain-lacking kinesin-related protein (SEQ ID NO:1), the 5' end was cloned from a human embryonic brain library (Clontech Laboratories Inc.) using a SMART RACE cDNA Amplification Kit from Clontech Laboratories Inc. The base sequence of the cloned DNA fragment was determined according to an established protocol (Sanger F. et al., Proc. Natl. Acad. Sci. USA 74:5463–5467 (1977)). The entire base sequences of both strands were analyzed.

The analysis results identified a DNA fragment for the known motor domain-lacking kinesin-related protein plus an additional 1390 base pairs at the 5' end. A search for the translation region of the fragment revealed an 85 base pair 5' end non-translation region, a 5472 base pair translation region and a 1353 base pair 3' non-translation region. The translated protein consisted of 1824 amino acids and had a molecular weight of 205,065 daltons. The amino acid sequence of the translated protein is set forth in SEQ ID NO:2, and the base sequence of the translation region is set forth in SEQ ID NO:4. This novel kinesin-related protein was designated as KIF1b-β. The base sequence set forth in SEQ ID NO:4 has been registered with the DNA Database of Japan (DDBJ), GenBank® brand computerized storage and retrieval services dealing with information relating to nucleic acid sequence data and EMBL Nucleotide Sequence Database (aka EMBL Bank) (Accession No.: AB017133).

Example 2

Measurement of Gene Expression in Human Neuroblastomas With Good and Unfavorable Prognosis by Semi-quantitative PCR PCR primers were synthesized from portions of the KIF1b-β gene and used for comparative measurement of expression in neuroblastoma clinical tissue samples with favorable prognosis and unfavorable prognosis. The sequences of the synthesized PCR primers are set forth in SEQ ID NO: 5 (forward primer) and SEQ ID NO: 6 (reverse primer). mRNA was extracted from human neuroblastoma clinical tissue samples and subjected to PCR reaction using rTaq (Takara Shuzo). Specifically, 5 µl of sterile distilled water, 2 µl of the mRNA, 1 µl of 10× rTaq buffer, 1 µl of 2 mM dNTPs, 0.5 µl each of the synthesized primer set and 0.5 µl of rTaq were combined. The mixture was denatured at 95° C. for 2 minutes and then a cycle of 95° C. for 15 seconds, 63° C. for 15 seconds and 72° C. for 20 seconds was repeated for 35 cycles, followed by 6 minutes of standing at 72° C. to complete the PCR reaction. The reaction solution was electrophoresed on 2.5% agarose gel. The results are shown in FIG. 1A and FIG. 1B.

The results in FIG. 1 confirmed enhanced expression of the KIF1b-β gene only in human neuroblastoma with favorable prognosis.

Example 3

Studies on Effects of KIF1b-β Gene and Motor Domain-lacking Kinesin-related Gene on Tumor Growth by Genetic Suppressor Element (GSE) Method (1)

Figure 2:
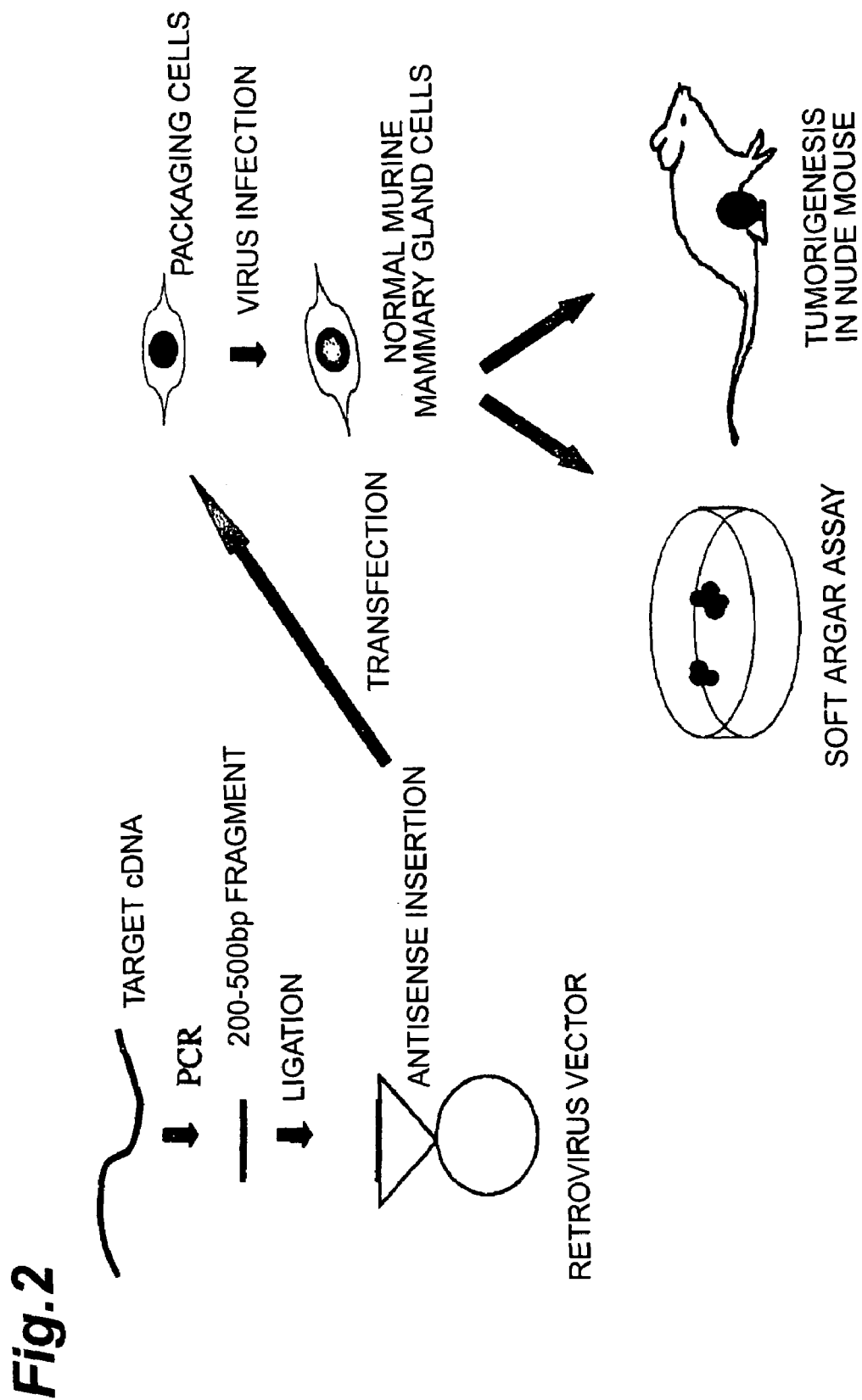
FIG. 2 is a schematic drawing of the GSE method used in the Examples.

"GSE" refers to a short biologically active gene fragment encoding a dominantly acting peptide or inhibitory antisense RNA. The method employing GSE as a tool in molecular oncology is known as the GSE method, and its concept and strategy is summarized in Roninson IB et al., Cancer Res. 55:4023–4028 (1995). Specifically, the GSE method may be applied for functional analysis of any gene in connection with tumor growth. The technique involves gene transfer into a receiving cell using a retrovirus vector and packaging cell, and determining the presence or absence of tumorigenesis. FIG. 2 shows an overview of this technique in sequence. More specifically, antisense to the gene of interest is inserted into the receiving cells, resulting in suppression of the gene function in the cells. Consequently, if the antisense-inserted cells acquire tumorigenic qualities, such as anchorage-independent growth, it may be concluded that the original function of the gene exerts negative control on tumorigenesis.

Following the protocol of Garkavtsev et al. (Garkavtsev I. et al., Nature Genet. 4, 415–420 (1996)), a retrovirus vector was constructed to express antisense to the KIF1b-β gene (KIF1b-β) and the motor domain-lacking kinesin-related gene (also referred to as "KIFAS"), and was used for transfection of murine mammary gland cells. The antisense sequence used is set forth in SEQ ID NO: 7. The antisense was ligated to a synthetic adapter, and the sense strand of the adapter was used as a PCR primer for PCR amplification. The PCR-amplified DNA was cloned in a retrovirus vector pLXSN, and the obtained plasmid library was transfected into BOSC23 virus packaging cells. Murine mammary gland cells (non-tumorized, immortalized murine mammary gland cells: NMUMG) were infected with the retrovirus-containing culture supernatant liquid. The infected murine mammary gland cells were cultured on soft agar medium (soft agarose gel) and the presence of anchorage-independent growth was observed. As a (negative) control there were used murine mammary gland cells with a neomycin resistance gene inserted in the same manner. The soft agar medium used was comprised of a lower layer (DMEM, 10% FCS, 0.6% agar) and an upper layer (DMEM, 10% FCS, 0.3% agar), and $5 \times 10^4$ of the cells were transferred to the soft agar medium (10 cm plate) and allowed to stand at 37° C. for 6–7 weeks. The observation results are shown in FIG. 3A (KIFAS-inserted cells) and FIG. 3B (negative control).

Figure 3B:
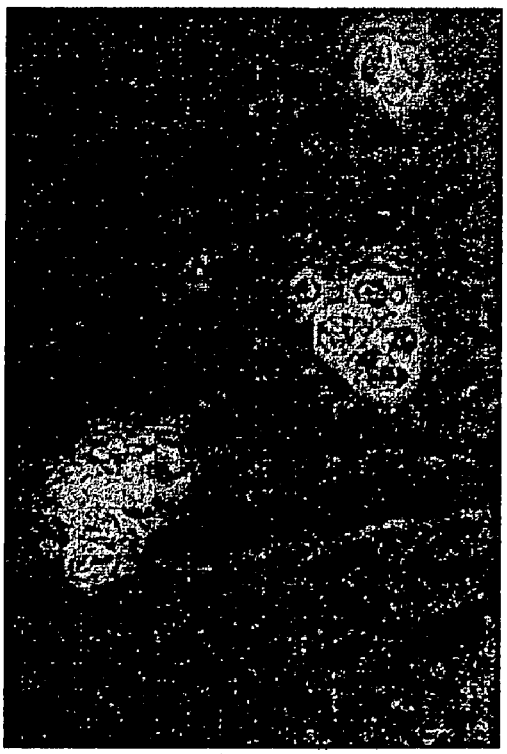
FIG. 3B is a representation corresponding to the photograph of soft agarose gel showing the results of anchorage-independent growth of murine mammary gland cells having a neomycin resistance gene inserted therein as a negative control using a retrovirus vector.
Figure 3A:
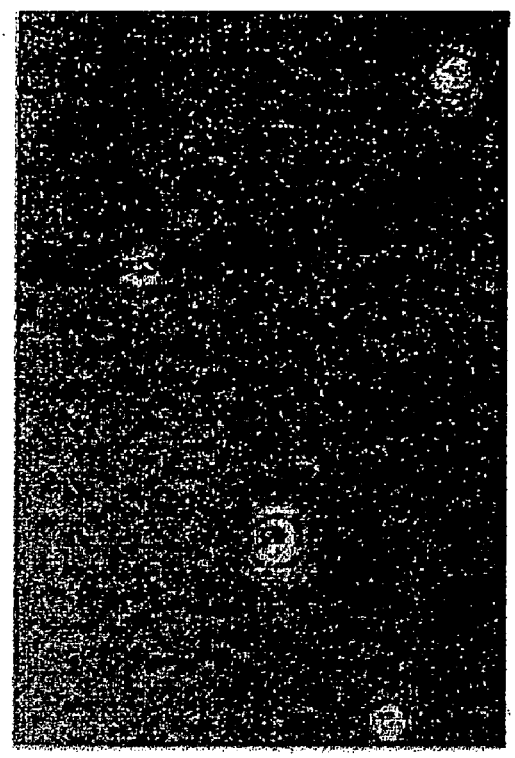
FIG. 3A is a representation corresponding to the photograph of soft agarose gel showing growth as a result of anchorage-independent growth of murine mammary gland cells having the KIF1b-β gene and a motor domain-lacking kinesin-related gene antisense (KIFAS) inserted therein using a retrovirus vector.

As shown by the results in FIG. 3A and FIG. 3B, marked anchorage-independent growth was observed in the KIFAS-transformed murine mammary gland cells as compared to the negative control.

Figure 4:
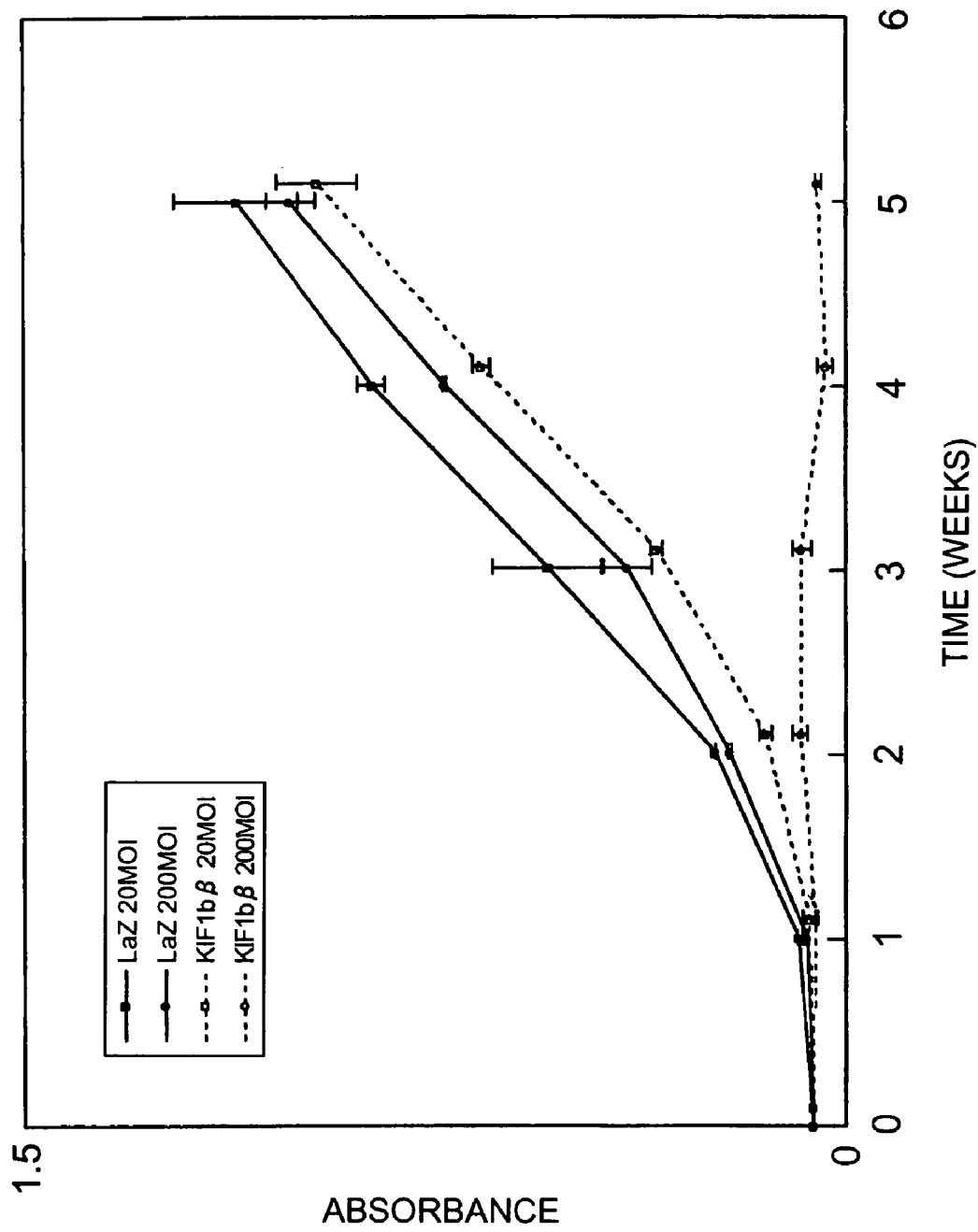
FIG. 4 is a graph showing growth curves for NMuMG cancer cells having the KIF1b-β gene inserted therein using an adenovirus vector.

In the same manner as above, the full-length cDNA for the KIF1b-β gene (SEQ ID NO: 4) was inserted into an adenovirus vector and used to infect NMuMG breast carcinoma cells. The cells were grown in medium and the growth curve was determined, as shown in FIG. 4. As a control, there were used NMuMG breast carcinoma cells infected with a vector containing only the LacZ promoter. In the drawing, "MOI" represents the number of viruses for infection per cell.

The full-length cDNA for the KIF1b-β gene was also inserted into an adenovirus vector and used to infect NB-C201 cells (a homozygous-deficient, or KIF1b-β gene-lacking neuroblastoma cell line). The cells were grown in medium and the growth curve was determined, as shown in FIG. 5.

Figure 5:
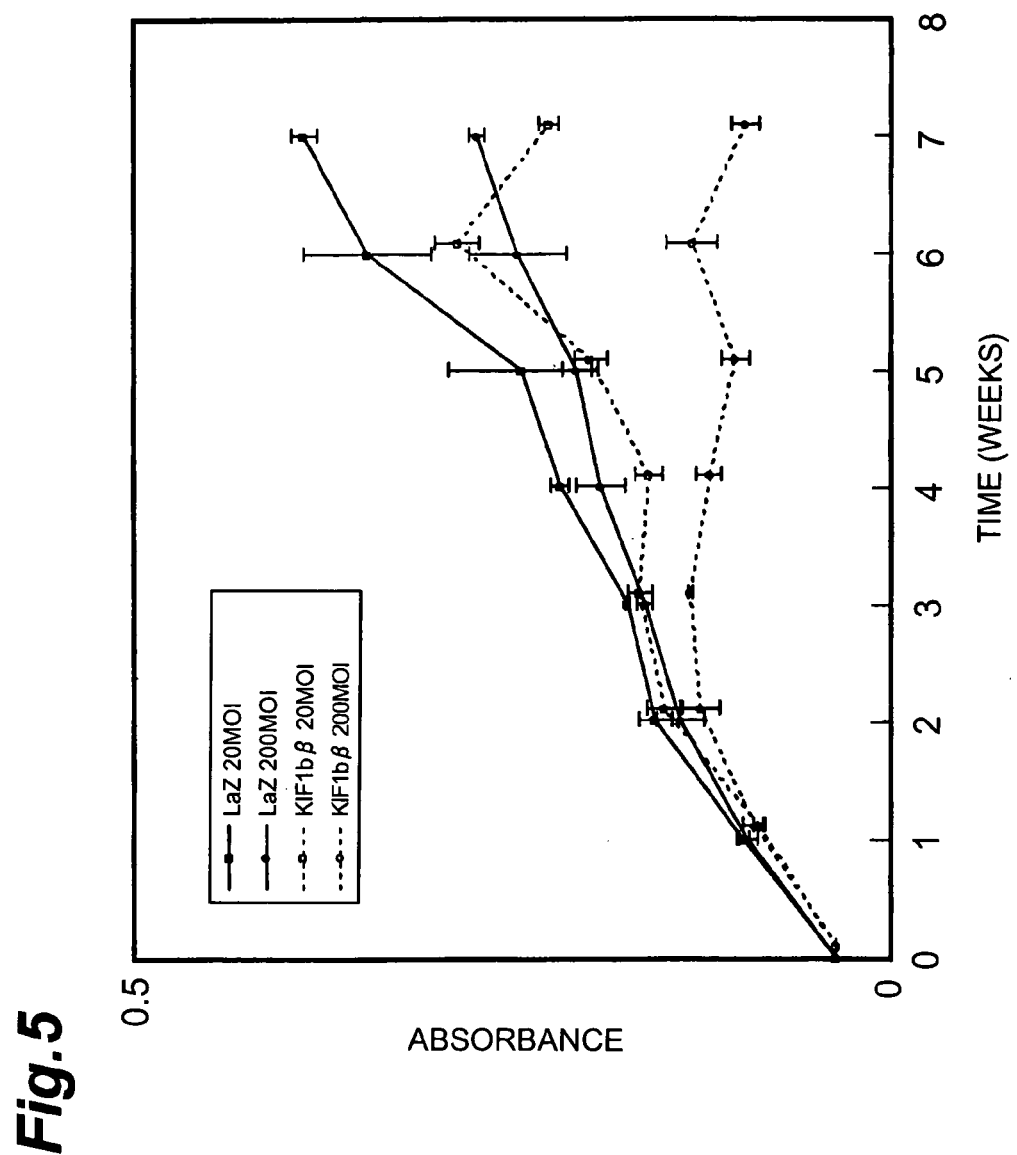
FIG. 5 is a graph showing growth curves for NB-C201 cells having the KIF1b-β gene inserted therein using an adenovirus vector.

Both FIG. 4 and FIG. 5 show that introduction of the KIF1b-β gene suppresses cancer cell growth.

Example 4

Studies on Effects of KIF1b-β Gene and Motor Domain-lacking Kinesin-related Gene on Tumor Growth by GSE Method (2)

Using the same method as described in Example 3, murine mammary gland cells infected with a KIFAS expressing retrovirus vector were transplanted under the femoral skin of a nude mouse, and the presence or absence of tumorigenesis was confirmed. As a (negative) control, there were used murine mammary gland cells having a neomycin resistance gene inserted in the same manner as Example 3, and these were also transplanted under the skin of a nude mouse. The results are shown in FIG. 6A (KIFAS-inserted) and FIG. 6B (negative control).

Figure 6B:
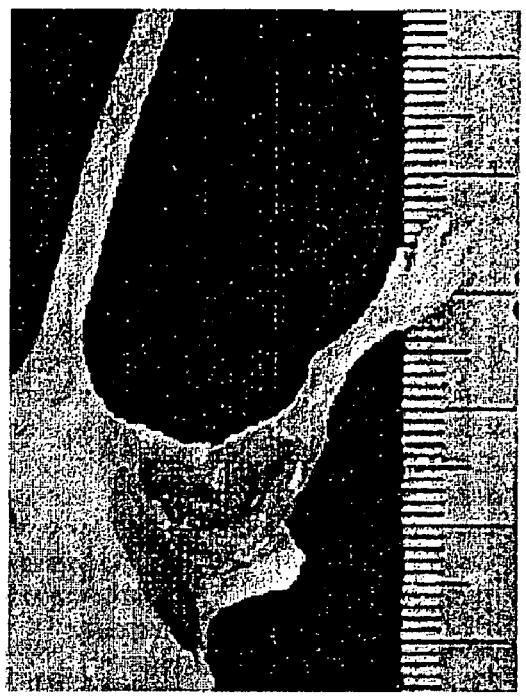
FIG. 6B is a representation corresponding to the photograph showing the results of nude mouse femoral subcutaneous transplantation of murine mammary gland cells having a neomycin resistance gene inserted therein as a negative control.
Figure 6A:
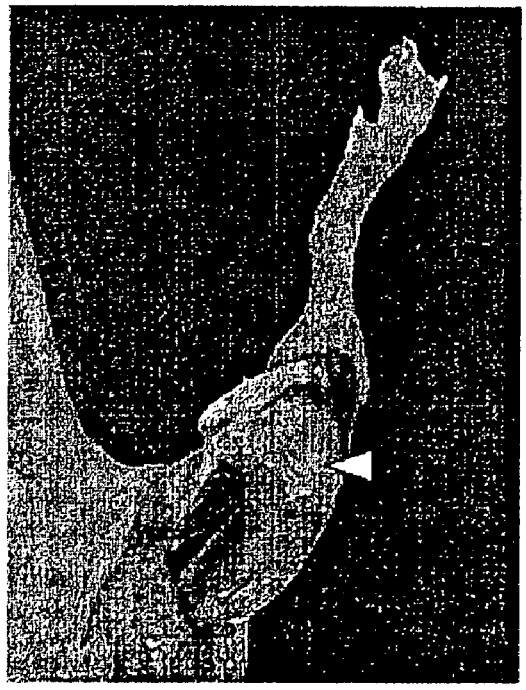
FIG. 6 is a representation corresponding to the photograph owing tumorigenesis as a result of nude mouse femoral subcutaneous transplantation of murine mammary gland cells having KIFAS inserted therein using a retrovirus vector.

As shown by the results in FIG. 6A and FIG. 6B, marked tumorigenesis was observed when the KIFAS-transformed murine mammary gland cells were transplanted under the femoral skin of the nude mouse, as compared to the negative control.

Figure 7:
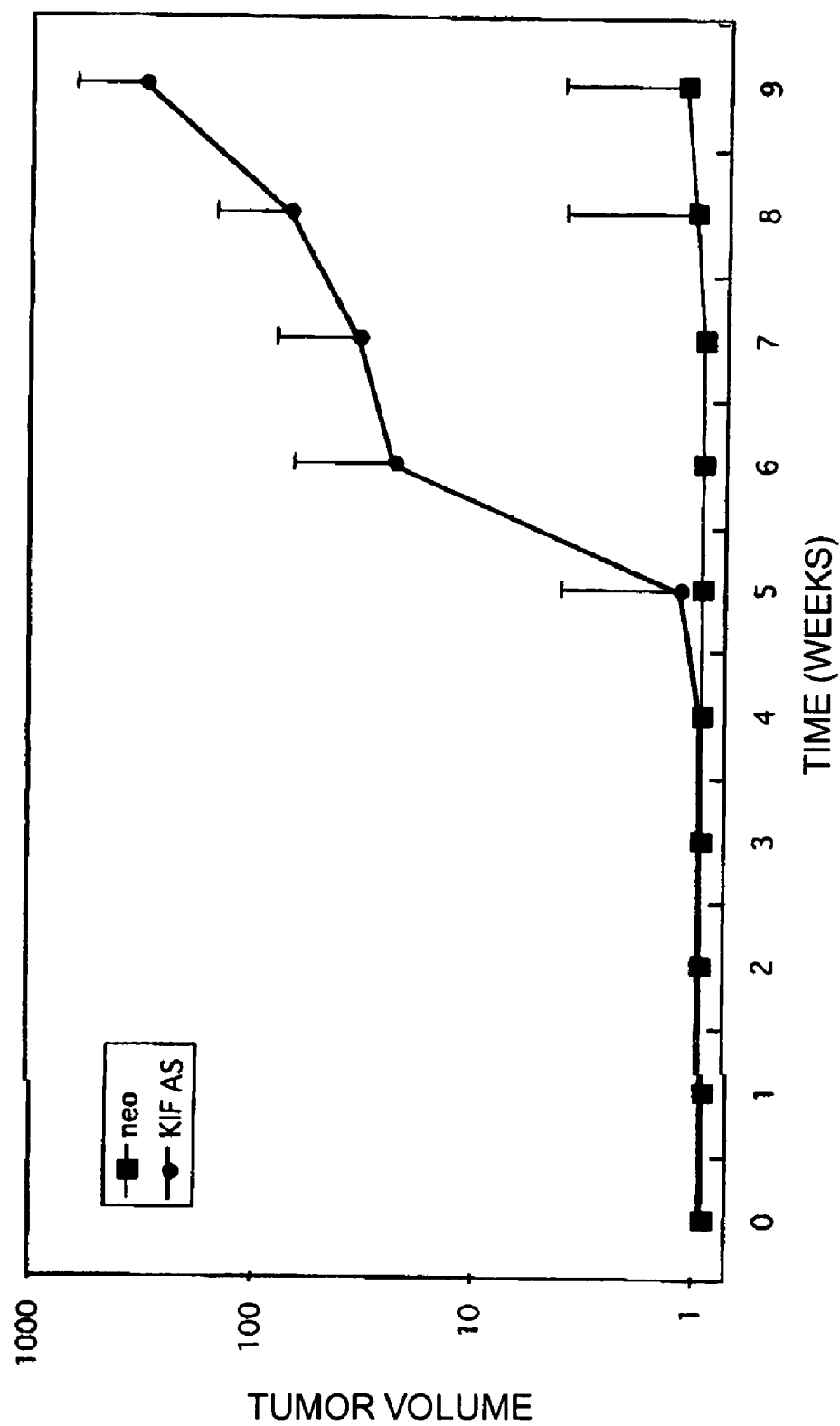
FIG. 7 is a graph of the mouse tumorigenesis shown in FIG. 6A, with tumor size (tumor volume) plotted against time.

KIFAS-transformed murine mammary gland cells and neomycin resistance gene-inserted murine mammary gland cells were also transplanted into 5 nude mice each of a treated group and a control group, and the changes in the sizes of the formed tumors were measured. The results are shown in FIG. 7, which clearly shows an increase in tumor size during the 5 weeks after transplantation in the treated group.

INDUSTRIAL APPLICABILITY

The nucleic acids of this invention are DNA or RNA for novel kinesin-related genes with a motor domain, which elucidate the base sequence data of the kinesin-related genes.

The nucleic acids of this invention or their fragments may be used as probes or primers for various types of hybridization or PCR toward detection of expression of the kinesin-related genes in tissues or cells and analysis of their structures and functions. The kinesin proteins encoded by the genes may be produced by genetic engineering.

Moreover, since expression of the nucleic acids of the invention is enhanced only in neuroblastoma clinical tissue with favorable prognosis, the prognosis of neuroblastoma may be diagnosed based on their level of expression.

It was confirmed that suppressing expression of the KIF1b-β gene and the motor domain-lacking kinesin-related gene with antisense nucleic acids according to the invention promotes anchorage-independent growth of normal cells which inherently only grow in an anchorage-dependent manner. That is, it was demonstrated that the genes function to suppress canceration of normal cells. It was also further discovered that introducing the KIF1b-β gene into cancer cells suppress growth of the cells. Based on these findings, the nucleic acids, proteins, etc. of this invention may be used as anticancer agents for treatment of malignant tumors, for the purpose of suppressing canceration of cells.

The invention claimed is:

1. An isolated nucleic acid having the base sequence set forth in SEQ ID NO:4 in the Sequence Listing.

2. An isolated nucleic acid having a base sequence encoding a protein comprising the amino acid sequence set forth in SEQ ID NO:2 in the Sequence Listing.

3. An isolated nucleic acid consisting of the base sequence set forth in SEQ ID NO:7 in the Sequence Listing or the full complement thereof.

4. An isolated protein having the amino acid sequence set forth in SEQ ID NO:2 in the Sequence Listing, or a pharmaceutically acceptable salt thereof.

* * * * *